(12) United States Patent
Zhang et al.

(10) Patent No.: US 6,235,504 B1
(45) Date of Patent: *May 22, 2001

(54) METHODS FOR IDENTIFYING GENOMIC EQUIVALENT MARKERS AND THEIR USE IN QUANTITATING CELLS AND POLYNUCLEOTIDE SEQUENCES THEREIN

(75) Inventors: Linqi Zhang, New York, NY (US); Sharon R. Lewin, Armadale (AU); Leondios Kostrikis, New York; David D. Ho, Chappaqua, both of NY (US)

(73) Assignee: The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/481,288

(22) Filed: Jan. 11, 2000

Related U.S. Application Data

(60) Provisional application No. 60/115,432, filed on Jan. 11, 1999.

(51) Int. Cl.[7] .............................. C12P 19/34; C12Q 1/68; C07H 21/02; C07H 21/04; C07H 21/00

(52) U.S. Cl. ..................... 435/91.2; 435/91.1; 536/23.1; 536/24.3; 536/24.31; 536/24.32; 536/24.33; 536/25.32

(58) Field of Search ..................... 435/6, 91.1, 91.2; 536/23.1, 24.3, 24.31, 24.32, 24.33, 25.32

(56) References Cited

FOREIGN PATENT DOCUMENTS

| 745690 | 12/1996 | (EP) . |
| WO98/10096 | 3/1998 | (WO) . |

OTHER PUBLICATIONS

Tyagi et al., 1996, Nature Biotechnology 14:303–8.

von Schwedler et al., 1990, Nature 345:452–6.

Douek et al., 1998, Nature 396:690–5.

Kostrikis et al., 1998, NatureMedicine 4:350–3.

Kostrikis et al., 1998, Science, 279:1228–9.

Finch et al Biotechniques vol. 21 No. 6 pp. 1055–1060 1996.*

\* cited by examiner

*Primary Examiner*—Kenneth R. Horlick
*Assistant Examiner*—Jeffrey Siew
(74) *Attorney, Agent, or Firm*—Klauber & Jackson

(57) ABSTRACT

Methods for identifying genetic sequences useful as genomic equivalent markers for organisms are described. The method involves determining the ratio of the absolute number of copies of wild type and mutant amplicons in a number of samples from organisms heterozygous for the mutation. After establishing the number of copies of a particular genetic sequence per genome, the sequence may be used as a measure of the number of genomes per sample, in order to normalize the analysis of another target sequence to abundance per cell. By way of example, the CCR5 gene was shown to be present at 2 copies per genome, and used to measure the number of copies per cell of HIV-1 provirions, human herpesvirus-8, and α deletion circles, a measure of recent thymic emigrants for assessing immune reconstitution. The genomic equivalent marker may be use to identify other genomic equivalent markers based on their copy number in proportion to a previously established marker; by way of example the copy number of the β-actin gene was found to be 16 copies per genome. The genomic equivalent marker may also be use to determine number of cells in a sample, such as from a tissue sample.

22 Claims, 8 Drawing Sheets

FIG. 3

SEQ ID No:1. CCR5 amplicon

GCTGTGTTTGCGTCTCTCCCAGGAATCATCTTTACCAGATCTCAAAAAGAAGGTCTT
CATTACACCTGCAGCTCTCATTTTCCATACAGTCAGTATCAATTCTGGAAGAATTTC
CAGACATTAAAGATAGTCATCTTGGGGCTGGTCCTGCCGCTGCTTGTCATGGTCATC
TGCTACTCGGGAATCCTAAAAACTCTGCTTCGGTGTCGAAATGAGAAGAAGAGGCAC
AGGGCTGTGAG

GATGGAAAACACAGTGTGACATGGAGGGCTGAACTTATTGCAACTCGT**GAGAACGGT
GAATGAAGAGCAGACA**GGGCCCGTGCCAGCTGCAGGGTTTAGGCACGGGGTGCAGGT
GCCTATGCATCACCGTGCACAGGAGTGGGCACCTTTACAAAAACCAGAGGTGTCAGC
ATGGTTGAAAGGATGTGGCATCACCTTTGTTGACAG (SEQ. ID NO:4)

GGATGGAAAACACAGTGTGACATGGAGGGCTGAACTTATTGCAACTCGT**GAGAACGG
TGAATGAAGAGCAGACA**GGGCCCGTGCCAGCTGCAGGGTTTAGGCACGGGGTGCAGG
TGCCTATGCATCACCGTGCACTGTGCTGAGGGGCTTTGCAAAAACCTGTGGCATCAG
CTTAACGAACCCTGCTTTGCAGAGCTTCCCAAGAACTAGAATTTTTCTCCAACTTCT
AAGCTTTAGAGGAAGGATAAGTCATGGTATCTTTCTTTCCAGTAGCCTAGGGCTTCA
GGCCTGAC (SEQ. ID NO:9)

FIG. 11

**Change in α1 Circles per $10^6$ PBMC on HAART:
Mean Slope ± S.D. (year$^{-1}$)**

| Baseline α1 circles/$10^6$ PBMC | Acute | Chronic |
|---|---|---|
| > 2200 | -0.16 ± 0.36 | -0.16 ± 0.50 |
| ≤ 2200 | 0.51 ± 0.46 | 1.49 ± 1.43 |

METHODS FOR IDENTIFYING GENOMIC EQUIVALENT MARKERS AND THEIR USE IN QUANTITATING CELLS AND POLYNUCLEOTIDE SEQUENCES THEREIN

This application claims benefit of Provisional No. 60/115,432 filed Jan. 11, 1999.

BACKGROUND OF THE INVENTION

Facile detection and quantitation of particular nucleic acid sequences in biological samples using various methodologies offers the healthcare field new research and diagnostic capabilities that extend from the identification of the underlying genetic basis of disease to identifying pathogens and monitoring the effectiveness of therapies to both infectious and noninfectious diseases. As new nucleic acid targets for measurement are identified and correlated with particular dysfunctions, increasing need has evolved in the sensitivity and accuracy of the detection methodologies, as well as the ability to perform assays rapidly and automatedly. Most detection methodologies employ nucleic acid amplification procedures such as PCR, with various means for detecting particular amplified sequences that may be present in a sample, such as the use of labeled, hybridizable probes. PCR may be performed in various formats, such as competitive and real time. Of particular note is the combination of real-time PCR with one or more fluorescent probes referred to as molecular beacons, which fluoresce at a particular wavelength only when hybridized to a particular target sequence, which may differ from another, unrecognized sequence by only a single nucleotide, as described by Tyagi et al., 1996, Nature Biotechnology 14:303–8; European Patent Application EP 745690; and International Patent Application WO 98/10096, incorporated herein by reference.

One application of the methodologies described above is in determining the abundance of one or more particular nucleic acid sequences in a cellular sample, and in particular, the abundance of the particular sequence(s) on a per cell basis in the sample. In order to determine the number of cells from which the nucleic acid sample is derived, various procedures have been used. These include such burdensome methods as counting the number of cells prior to the preparation of nucleic acid from the cells, or using a more readily measurable marker of the number of cells from which the sample is derived. For example, the amount of DNA per cell may be determined, then the amount of DNA in a sample measured and extrapolated to the number of source cells. This procedure is inaccurate and moreover, burdensome, as these and other procedures require the concurrent determination of cell number utilizing a different procedure than the nucleic acid quantification procedure also to be applied to the sample. Methods have been developed in which the number of input cells have been determined by measuring a particular genomic nucleic acid sequence in the sample, such as that of the β-actin and glyceraldehyde-3-phosphate dehydrogenase (GAPDH) genes. However, the number of copies of the genes for these proteins is unknown and pseudogenes exist, and as such the denotation of the number of copies of the target nucleic acid per genome is not on a per genome basis and thus, may not be accurate.

As mentioned above, the need for accurately determining the number of copies of a particular nucleic acid sequence per cell in a biological sample has important utility in uncovering relationships between nucleic acid sequence abundances and dysfunctions, as well as diagnosing and monitoring therapies. Such sequences may be genomic or extrachromosomal, including viral, microbial or cellular. For example, a diagnostically important value is the number of infectious particles per cell, such as viruses and proviruses (HIV-1, Kaposi's sarcoma virus [human herpesvirus 8], hepatitis B and C, for example), bacteria (mycobacteria, for example), fungi, and parasites (malaria and Leishmania, for example). Other diagnostically important assessments include non-infectious agents. One particular utility is in the assessment of thymic function. The thymus is a lymphoid organ serving as the site for T cell differentiation, enlarging during infancy, stabilizing until puberty, then declining in size, and believed until recently, in function, after the third decade. Measurement of thymic function is an indicator of the ability of the immune system to recover from or become reconstituted after therapies which destroy immune cells, such as chemotherapy or radiotherapy, and to monitor the course of diseases and therapies directed thereto in infectious and noninfectious diseases involving the immune system, such as HIV-1 infection, congenital immunodeficiency disorders, as well as iatrogenically-induced immunodeficient states, for example, by radiotherapy or chemotherapy for the treatment of dysproliferative diseases. The numbers of lymphocytes in the blood that are of recent thymic origin is a measure of the output of newly generated T cells from the thymus. The numbers lymphocytes in the blood may be determined by detecting in nucleic acid isolated from peripheral blood mononuclear cells (PBMCs) the abundance of a particular species of extrachromosomal DNA formed during the excisional rearrangement of T cell receptor (TCR) genes. In the formation of αβ and γδ cells (bearing unique TCRs), excisional circles called a deletion circles and δ deletion circles, respectively, are formed (von Schwedler et al., 1990, Nature 345:452–6). As shown recently by Douek et al. (1998, Nature 396:690–5), measurement of a circles in normal subjects from birth to 73 years of age using quantitative competitive PCR showed sustained output of T cells from the thymus. Furthermore, HIV-1-infected individuals showed suppressed thymic function, but after undergoing highly active antiretroviral therapy, showed a rise in the number of a circles in CD4+ cells. These studies established the value in monitoring thymic function using TCR gene deletion circles, without precisely determining the abundance of such circles on a per cell basis. Thus, an important addition to the knowledge of an HIV-1 patient's viral load and CD4+ cell count would be thymic function as described above.

Other conditions in which immune recovery or reconstitution is an important parameter for monitoring therapies, such as bone marrow transplant, for congenital immunodeficiency disorders, such as DiGeorge syndrome, characterized by absence or hypoplasia of the thymus and a partial or complete T cell (but not B cell) deficiency. Furthermore, recovery from induced immunodeficiencies, for example, cancer treatment, using radiation and/or chemotherapeutic agents, may be monitored by assessing recent thymic emigrants. To follow individual patients, determine precise relationships between stages of disease and thymic function, and to establish normal and abnormal ranges, normalization of TCR circles on a per cell basis is necessary.

The abundance of other nucleic acid sequences expressed on a per cell basis is also important for following the status of individual patients, determining precise relationships between stages of disease and recover with particular sequences, and to establish normal and abnormal ranges. Thus, both longitudinal and cross-sectional studies of individuals may be performed to monitor individuals and establish correlations.

A further utility of genetic sequences of a known number of copies per cell is in the determination of cell numbers from biological samples, particularly when assessment methods involving gene amplification or other genetic methods are used for the analysis. For example, determining the number of cells such as leukocytes or germ cells such as sperm in a bodily fluid sample or the number of cells in a tissue sample may be determined by nucleic acid assessment methods by determining the number of copies of a particular genetic sequence known to exist at a fixed number of copies per cell.

It is thus toward a method for identifying genetic sequences suitable for use as genomic equivalent markers present at a particular copy number per genome, and the utility of the marker in determining numbers of cells and the number of copies per cell of a particular nucleic acid sequence that the present invention is directed.

The citation of any reference herein should not be construed as an admission that such reference is available as "Prior Art" to the instant application.

SUMMARY OF THE INVENTION

In accordance with the present invention, method is provided for identifying a genetic sequence in an organism suitable for use as a genomic equivalent marker comprising the steps of (1) selecting a gene known to occur as both a wild type and in at least one mutant allele form in said organism, and having wild type homozygotes, mutant homozygotes, and heterozygotes of said organism; (2) determining the relative numbers of copies in the heterozygotes of said organism of the wild type and mutant sequences;(3) correlating a ratio of one wild type gene to one mutant gene in said heterozygous genome with the existence of a single allele for said gene; and (4) identifying said gene as existing as two copies per genome and as a genomic equivalent marker with two equivalents per genome. The method for identifying the number of copies of said genes may be performed using molecular beacons in combination with real-time PCR.

The present invention if also directed to a method for identifying a preselected gene in an organism as being suitable for use as a genomic equivalent marker comprising the steps of: (1) selecting a candidate preselected gene in the genome of said organism; (2) identifying a first genomic equivalent marker in said organism in accordance with the method described above; (3) identifying the relative number of copies of said preselected gene in a sample of genomic DNA and the relative number of copies of said first genomic equivalent marker; and (4) identifying said preselected gene as a genomic equivalent marker with a copy number per cell equal to the ratio of the copy number of said preselected gene to the copy number of the gene of said first genomic equivalent marker. A non-limiting example is provided wherein said first genomic equivalent marker is CCR5.

A method for determining in a nucleic acid sample of cellular origin the number of copies per cell of at least one preselected polynucleotide target sequence is provided herein, comprising quantifying in said sample the abundance of said at least one target sequence, quantifying in said sample the abundance of at least one genomic equivalent marker sequence, and expressing said number of copies of said at least one target sequence per cell as a ratio between said abundance of said target sequence and said abundance of said at least one genomic equivalent marker.

The genomic equivalent marker described above may be, for example, CCR5 and β-actin. The quantifying of said at least one target sequence and of said at least one genomic equivalent marker sequence may be performed using real-time PCR amplification in combination with molecular beacons. To utilize CCR5 as the genomic equivalent marker, amplification primers SEQ ID NO:2 and SEQ ID NO:3 may be used, as non-limiting examples, and an example of a molecular beacon in that with a sequence of SEQ ID NO:4, and in particular, the following structure: Tetramethylrhodamine-GCGCCTATGACAAGCAGCGGCAGGAGGCGC-DABCYL SEQ ID NO:4.

The genomic equivalent marker of the present invention may be used to determine the number of copies of a marker of thymocyte proliferation, for example, the number of T cell receptor gene DNA deletion circles. The circles may be α1 circles, α2 circles, δ1 circles, δ2 circles, δ3 circles, δ4 circles, δ5 circles, and combinations thereof. Preferably, α1 circles are measured, and further, in combination with α2 circles. The quantifying of α1 circles is performed using primers, as nonlimiting examples, SEQ ID NO:6 and SEQ ID NO:7 and a molecular beacon with a sequence of SEQ ID NO:8, with a structure: Fluorescein-CGAGGCGAGMCGGTGAATGMGAGCAGACAGCCTC G-DABCYL SEQ ID NO:8. α2 circles may be quantified by the methods of the present invention using primers, for example, SEQ ID NO:6 and SEQ ID NO:10 and a molecular beacon with a sequence of SEQ ID NO:8. Furthermore, the invention may be used to determine the number of target sequences of a pathogen, such as a provirus, virus, bacterium, fungus, or parasite.

The quantitation of the target sequence and the genomic equivalent marker may be performed simultaneously.

A non-limiting example of the practice of the present invention provides for a method for determining in a nucleic acid sample of cellular origin the number of copies per cell of at least one preselected polynucleotide target sequence comprising quantifying in said sample the abundance of said at least one target sequence, quantifying in said sample the abundance of at least one genomic equivalent marker sequence, and expressing said number of copies of said target sequence per cell as a ratio between said abundance of said target sequence and said abundance of said genomic equivalent marker, comprising the steps of:

a. providing a nucleic acid sample derived from a sample of cellular origin in which said determining the number of copies per cell is desired;

b. providing forward and reverse primers for each of said at least one target sequences and said at least one genomic marker sequence;

c. providing a molecular beacon capable of binding to a subsequence within the target sequence for each of said at least one target sequence and said at least one genomic equivalent marker sequence;

d. incubating said nucleic acid sample, said primers and said molecular beacons together with the necessary components and under real-time PCR conditions to amplify said at least one target sequence and said at least one genomic equivalent marker sequence and to cause the interaction between said molecular beacons and said sequences present in said sample;

e. monitoring the change in fluorescence with time of each of said molecular beacons during said real-time PCR;

f. quantitating the abundance of any of said at least one target sequence in said sample and the abundance of said at least one genomic equivalent marker sequence by correlating the threshold cycle of each molecular beacon with a predetermined relationship between the threshold cycle and the quantity of the sequence; and g. expressing the number of copies of said at least one target sequence per cell as the ratio of the abundance of said at least one target sequence with the abundance of said at least one genomic equivalent marker.

In a further non-limiting example, at least one target sequence is α1 deletion circles and said at least one genomic equivalent marker is CCR5.

A kit is provided herein for determining in a nucleic acid sample of cellular origin the number of copies per cell of at least one preselected polynucleotide target sequence comprising the components of:

a. a forward and reverse primer and a molecular probe for each of said at least one target sequence and at least one genomic equivalent marker sequence;

b. means for performing an quantitating the results of real-time PCR c. instructions for use of the kit.

A preferred kit utilizes the genomic equivalent marker CCR5.

A method for also provided herein for enumerating cells in a biological sample comprising quantitating a genomic equivalent marker in said sample.

It is thus an object of the present invention to provide methods for identifying genomic equivalent markers, and further, to use a particular genomic equivalent marker to identify other genetic sequences suitable for use as other genomic equivalent markers.

It is also a principal object of the present invention to provide a genomic equivalent marker to facilitate the denotation of target cellular nucleic acid levels as abundance per cell.

It is a further object of the present invention to utilize the genomic sequence of CCR5, present at two copies per cell, as a genomic equivalent marker.

It is yet a further object of the present invention to provide enhanced measurement on a per cell basis of various nucleic acid sequences.

It is another object of the present invention to provide a method of determining the number of cells in a biological sample by determining the abundance of a genomic equivalent marker.

It is yet a further object of the present invention to assess the number of infectious particles or agents, such as proviruses, viruses, bacteria, fungi and parasites, on a per cell basis.

It is still a further object of the present invention to provide enhanced measurement on a per cell basis of DNA deletion circles derived during T cell receptor gene rearrangement, as an indicator of thymic function and of immune reconstitution.

These and other aspects of the present invention will be better appreciated by reference to the following drawings and Detailed Description.

BRIEF DESCRIPTION OF THE DRAWINGS

FIG. 3 depicts the amplicon for the CCR5 gene (SEQ ID NO:1), with the forward and reverse primers (SEQ ID NO:2 and SEQ ID NO:3, respectively) shown underlined and the sequence detected by the molecular beacon LK155 (SEQ ID NO:4) shown in bold.

FIG. 4 depicts the amplicon for the α1 circle (SEQ ID NO:5), with the forward and reverse primers (SEQ ID NO:6 and SEQ ID NO:7, respectively) shown underlined and the sequence detected by the molecular beacon LK159 (SEQ ID NO:8) shown in bold.

FIG. 5 depicts the amplicon for the α2 circle (SEQ ID NO:9), with the forward and reverse primers (SEQ ID NO:6 and SEQ ID NO:10, respectively) shown underlined and the sequence detected by the molecular beacon LK159 (SEQ ID NO:8) shown in bold.

FIG. 11 shows the effect of highly active antiretroviral therapy (HAART) on thymic functions as assessed by α1 circled per million PBMCs in chronically infected patients.

DETAILED DESCRIPTION OF THE INVENTION

Figure 1A:
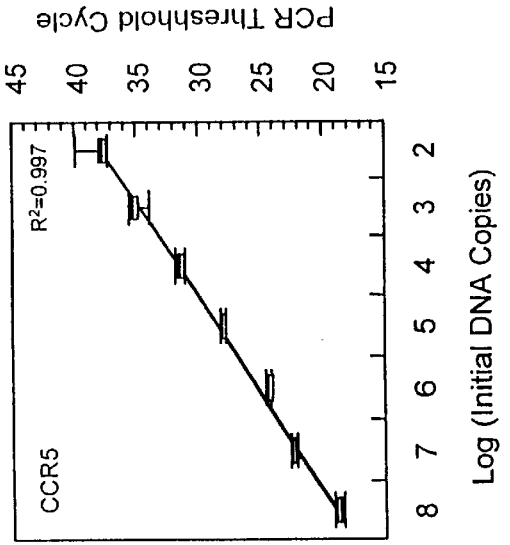
FIG. 1A shows the fluorescence versus PCR amplification cycle number for the CCR5 Δ32 amplicon over a range of input copies, and the corresponding standard curve relating input copy number to threshold cycle (FIG. 1B).
Figure 1B:
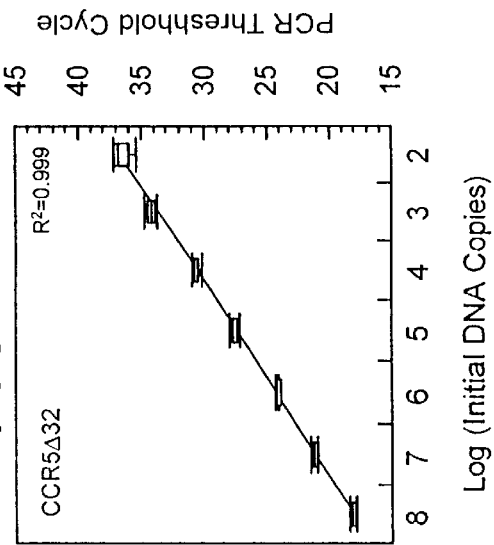
FIG. 1 depicts the determination of the cycle number and fluorescence, and the relationship between threshold cycle and initial input DNA copies, of the wild type (CCR5) and mutant (CCR5Δ32) amplicons from homozygous wild type and mutant individuals.
FIGS. 1C and 1D show the same results for the wild type amplicon, respectively.
Figure 1C:
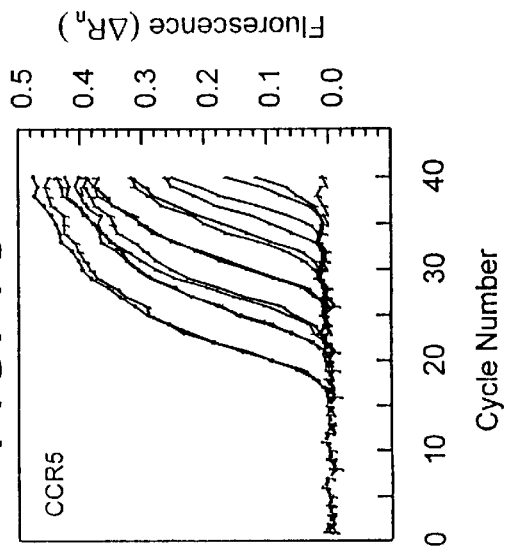
Figure 1D:
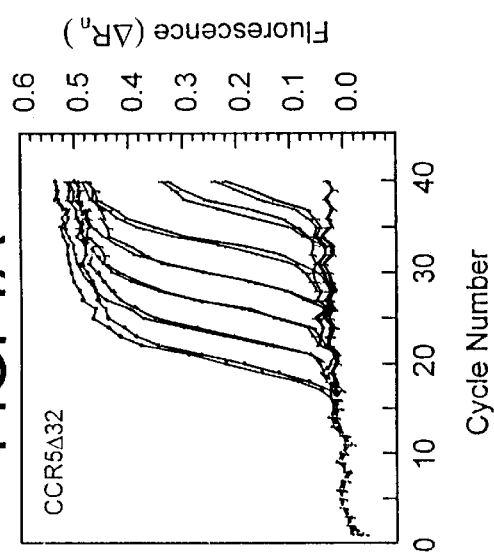

The following terms are used herein:

"Molecular beacon" is a nucleic acid probe that recognizes and reports the presence of a specific nucleic acid in homogeneous solutions. The probes are hairpin-shaped sequences with a central stretch of nucleotides complementary to the target sequence and termini comprising short mutually complementary sequences, one terminus covalently bound to a fluorophore and the other to a quenching moiety. When in their native state with hybridized termini, the proximity of the fluorophore and the quencher produce no fluorescence. The beacon undergoes a spontaneous fluorogenic conformational change when hybridized to its target nucleic acid.

"Real-time PCR" describes a polymerase chain reaction which is monitored, usually by fluorescence, over time during the amplification process, to measure a parameter related to the extent of amplification of a particular sequence, such as the extent of hybridization of a probe to amplified target sequences.

"Genomic equivalent marker" refers to a DNA sequence present invariantly in the cellular genome of an organism at a fixed number, such as one per haploid genome, or two per somatic cell, such that the number of copies of the marker in a sample of nucleic acid derived from cells, tissues, or other biological material of cellular origin can be equated precisely, i.e., normalized, to the number of cells from which the sample was derived. In the instance wherein two copies of the marker sequence are present in the cell, the number of cells would be half the number of marker sequences present in the sample. Other genomic equivalent markers may be present at greater frequencies than two per cell, and the ratio of the number of genomic equivalent marker sequences in a sample to the number of cells in the sample used to calculate the number of cells. For example, if a marker is present at 8 copies per genome, the number of sequences in a sample would be divided by eight to obtain the number of cells from which the sample was derived. Genomic equivalent markers may be identified in animals, plants, protists, eubacteria, archebacteria, and any other organism having a genome.

"CCR5" is an abbreviation for the human CC-chemokine receptor gene 5 which has been found by the inventors herein to exist at two copies per diploid cell, and thus one copy per haploid cell.

"α deletion circles" are among the various species of T cell receptor rearrangement excisional circles of DNA which form during the rearrangement of the T cell receptor gene. Other circles include α2, and during the formation of γδT cells, form δ1, δ2, δ3, δ4, and δ5 circles. The number of α deletion circles per cell in a sample is an indication of the number of events leading to the formation of new TCR, and thus of the number of naive T cells in the sample.

"Preselected polynucleotide target sequence" refers to a particular nucleic acid sequence, the abundance of which is to be determined.

It has been discovered herein that by using the existence of a mutant gene in a population of organisms, the number of copies of the gene in the genome of the organism may be determined. The quantitation of the gene may be done by any number of methods, and may measure the gene or a sequence contained within the gene such as an amplicon or target of a probe for a specific sequence within the amplicon or gene. As relates herein generally to the measurement of a gene or an amplicon or sequence contained within that gene, the terms gene, amplicon, and target sequence are used interchangeably. One important utility of this determination is that the identified gene and its copy number per genome (referred to herein as a genomic equivalent marker) may be used to identify the number of genomes, and hence cells, in a biological sample. In addition to providing a means for determining cell number, measurement of the genomic equivalent marker in combination with a preselected polynucleotide target sequence whose abundance is to be determined, the result may be denoted in terms of the number of copies of the predetermined polynucleotide sequence per genome or per cell. As will be noted below, ability to denote polynucleotide sequences on a per cell basis has important diagnostic utility.

By way of a non-limiting example, it was found herein that a polynucleotide sequence within the human CC-chemokine receptor gene 5 (CCR5) exists at two copies per cell. As such, the CCR5 gene, and in particular the sequence defined by the amplicon used herein, has utility as a marker to indicate the number of cells from which a sample of nucleic acid has been prepared, as each cell will contribute two copies of the CCR5 polynucleotide sequence to the sample. Other genes present at two copies per cell may also be identified by the methods described herein and used in an analogous manner as a genomic marker, hereinafter referred to as a genomic equivalent marker, as the number of copies of such a gene in a DNA sample is equivalent to twice the number of input cells. Furthermore, and as will be detailed below, once a first genomic equivalent marker has been found, another genomic equivalent marker may be identified based on its abundance in proportion to the first genomic equivalent marker, and then used itself as a genomic equivalent marker. As described in the background section above, the ability to express (i.e., denote) the number of copies of particular polynucleotide sequences of cellular origin as the number of copies present in a sample per cell has important diagnostic and therapeutic implications, and offers a heretofore unavailable precision in identifying changes in longitudinally-collected samples, as well as in distinguishing normal from abnormal ranges when such ranges are narrowly defined. Furthermore, the same analytical methodology applied to determining the abundance of the preselected target polynucleotide sequence may be utilized in determining the abundance of the genomic equivalent marker, thus simplifying the accurate and precise measurement of the target sequence on a per cell basis. As used herein, the terminology of denoting or expressing of the number of copies of a particular sequence on a per cell basis may also be termed normalization or standardization of the number of copies of a particular sequence on a per cell basis.

As will be seen below, the genomic equivalent marker also may be used in quantitating the number of cells in a biological sample. The methods for determining by genetic analysis, such as by PCR or other amplification procedures) the number of cells herein provides a means for automating and precisely determining cell numbers, methods which heretofore were reliant upon cumbersome counting methods or imprecise assumptions as to the metabolic or enzymatic activity of each cell within a population being measured. Furthermore, the cell counting method described herein may be automatedly integrated with other determinations being performed on the same cellular sample, in particular genetic analysis and as shown below, determination of particular polynucleotide sequences, to provide a facile determination of abundance per cell.

As shown in Example I, the existence of only two copies of the CCR5 gene per genome was found as a result of further investigations following studies quantitating the relative abundance of the CCR5 gene and a deletion mutation thereof referred to as Δ32 in the patient population and particularly its relationship to influence on the progression of HIV-1 disease (Kostrikis et al., 1998, Nature Medicine 4:350–3). The known Δ32 deletion within the CCR5 gene at a high enough frequency (~20% allele frequency in Caucasians) that permitted the ready acquisition of samples from individuals who are wild type homozygotes (both alleles are wild type), heterozygotes (one allele is wild type and the other contains the Δ32 deletion) and mutant homozygotes (both alleles have the Δ32). The genotyping of CCR5Δ32 in individuals can be perform by a variety of methods including the recently described technique called "spectral genotyping" (Kostrikis et al., 1998, Science 279:1228–9).

First, a set of PCR primers were designed (SEQ ID NO:2 (LK46) and SEQ ID NO: 3 (LK47)) such that the amplicon (SEQ ID NO:1) contains the putative Δ32 deletion. The two CCR5 alleles (wild type and mutant Δ32) in human PBMCs were then amplified by PCR using the two primers and template genomic DNA from individuals who are wild type homozygotes (both CCR5 alleles are wild type) and mutant homozygotes (both CCR5 alleles have the Δ32 deletion). The amplicons from the wild type and mutant cells were subsequently purified from unincorporated mononucleotides (dNTPs) and PCR primers by either several rounds of ethanol precipitation and resuspension in water or by filtering through specialized columns purchased from QIAGEN. The molar concentration of each purified amplicon was determined following well-established procedures by ultraviolet (UV) absorbance spectroscopy by (i) measuring the full absorbance spectra (220 to 320 nm) in a UV spectrophotometer (CARY 218), (ii) correcting for light scattering contributions at 320 nm, and (iii) assigning an extinction coefficient based on the base composition of the amplicon.

Subsequently, the correlation between the threshold cycle (derived by real time PCR [see Tyagi and Kramer, 1996, Nature Biotechnology 14:303–308] using the allele specific molecular beacons described above) and the initial concentration of DNA templates (six log dilutions from $10^8$ to $10^2$ molecules per PCR reaction) is determined. In the particular case of the CCR5 study described herein, the two standard curves are equivalent within experimental errors, indicating that any derived threshold cycle corresponds to the same number of either wild type or mutant (Δ32) amplicons. The exactness of the two standard curves is not a critical part of the method described herein as long as the precise measurement of the abundance of the wild type and the mutant sequence is determinable in genomic samples. In this particular case, the overall thermodynamic properties and molar concentrations of the molecular beacons and PCR primers, and the length of the amplicons are the same, resulting in nearly identical standard curves, and therefore making interpretation of the ratio of the two sequences easy to visualize and interpret.

Figure 2:
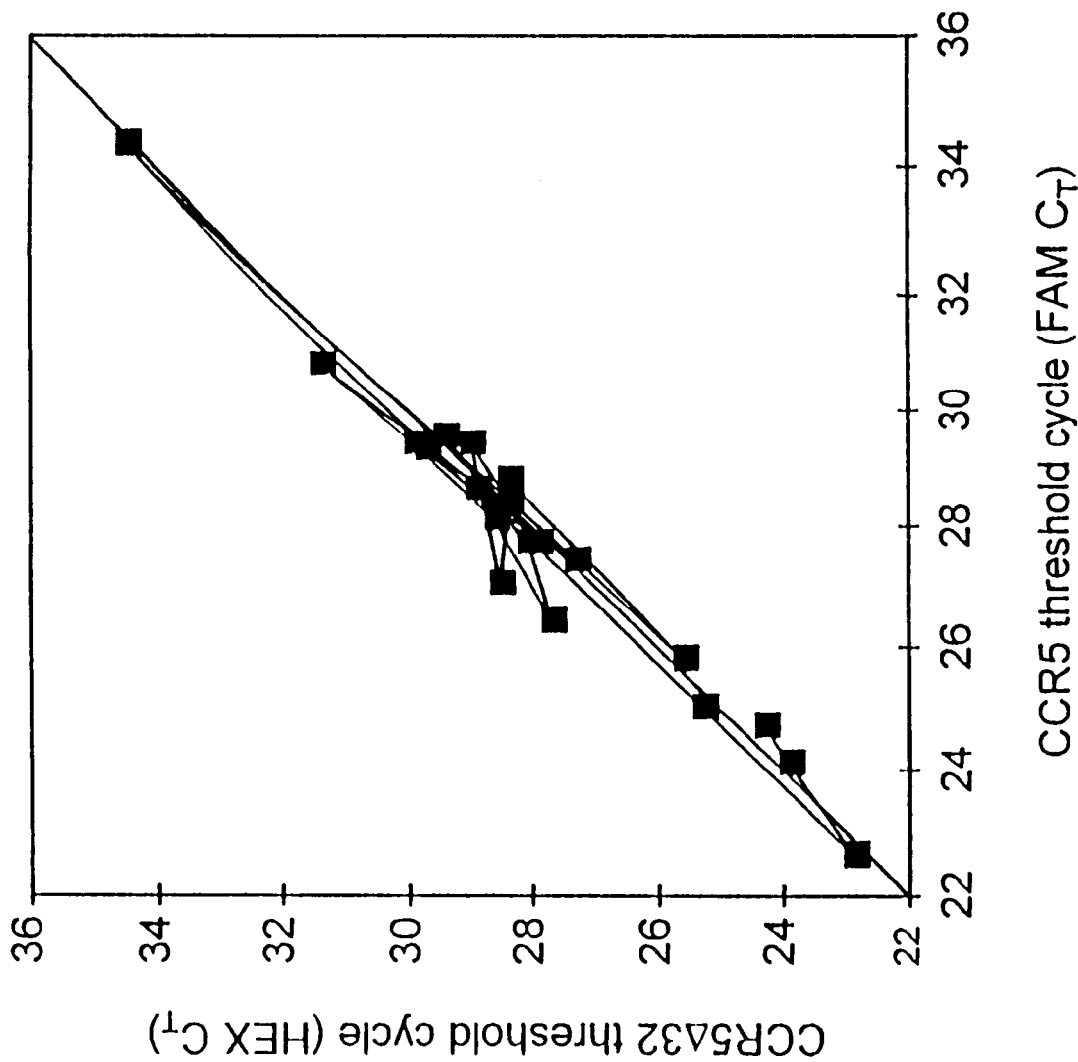
FIG. 2 shows the correlation between the threshold cycle of the CCR5 wild type amplicon and the CCR5Δ32 amplicon in heterozygous individuals.

In the next and final step, the ratio of wild type CCR5 and mutant CCR5Δ32 alleles was determined in a number of samples from heterozygotes (FIG. 2). This is carried out by plotting the threshold cycles measured from the wild type and mutant alleles in each individual, using the allele-specific molecular beacons as described above. The measurement of the threshold cycle for each sequence may be measured in a single assay, using a multiplexed real time PCR molecular beacon format with the molecular beacons for the wild type and mutant alleles separately quantifiable in the sample; alternatively, they may be measured separately.

As indicated by the results shown in FIG. 2, the ratio of wild type CCR5 to mutant CCR5Δ32 amplicons is one to one, indicating that the CCR5 amplicon defined by the two PCR primers exist in two copies per cell. This ratio would not be achieved if any other sequences in the genome were amplified by the particular primers and identified by the molecular beacons (i.e., pseudogenes), and thus confirms the existence of only two copies per genome.

Thus, the CCR5 gene, and in particular, the amplicon defined by the primers used herein, may be used as a genomic equivalent marker as the sequence is present at two copies per genome. Other genomic equivalent markers may be identified as present at two copies per genome following similar methods. A gene is selected which is known to be polymorphic (a mutant allele in which, for example, a deletion, point mutation, or insertion occurs) such that a wild type and mutant form exist, such that individual organisms that are homozygous for the wild type gene, homozygous for the mutant gene, and heterozygous for the gene are available for performing the same type of analysis as performed herein with CCR5 and the Δ32 mutant. Primers for an amplicon spanning the region containing the mutation, and molecular beacons specific for each of the wild type and mutant alleles, are prepared. The particular genetic sequence (amplicon) from the genomes of the two homozygous organisms are amplified and purified, and the UV molar extinction or other means for identifying the absolute number of input copies of the amplicons are determined. Using real-time PCR and molecular beacons, or an alternate method, correlations are obtained separately for the number of input copies of each of the wild type and mutant sequences, and the real-time PCT threshold cycle (usually selected to be the cycle number at which the molecular beacon is detectable by fluorescence of 10 standard deviations above background fluorescence). Once both the wild type and mutant sequences are quantifiable in a sample, the relative abundance of the wild type and mutant sequences are determined in samples derived from a population of individuals (organisms) heterozygous for the gene, and the relationship between the abundance of the wild type and mutant form are determined. A ratio of one to one indicates that two alleles exist in the genome, and that no pseudogenes (other wild type amplicons present in the genome) are present.

Once a genomic equivalent marker is identified (such as the CCR5 amplicon described hereinabove), it may be used directly as a marker for quantitating other preselected polynucleotide target sequences or cell numbers in biological samples. Another utility of a genomic equivalent marker determined by the procedures described herein in identifying other genomic equivalent markers, as will be elaborated below. In quantitating a preselected polynucleotide target sequence in a biological sample on a per cell or per genome basis, the molecular beacons used to determine the relative abundance of the wild type and mutant alleles of the genomic equivalent marker as described above may be used subsequently in determining the number of genomes in a sample. However, a preferable method to avoid needing to quantitate both the wild type and mutant alleles in a sample is accomplished by utilizing a sequence within the so-identified genomic equivalent marker amplicon which is identical in both the wild type and mutant genomes, i.e., a sequence away from the position of the mutation but still within the amplicon. In this preferred example, a molecular beacon that will identify the number of either wild type or mutant alleles in a sample will indicate a presence of two copies of the sequence per genome, and the number of cells therein derived half that number. Should the genomic equivalent marker sequence include the portion of the gene in which the mutant allele is present in the population, for example, if the frequency of the mutation is high and no sequence away from the mutation but still within the amplicon is suitable, the same two molecular beacons described above, to the wild type and the mutant form, may be used concurrently to identify the abundance of each form (wild type and/or mutant) of the alleles present in the sample. If the sample contains only wild type sequences or only mutant sequences, only the wild type or the mutant sequences, but not both, will be present at two copies per genome. If the sample if derived from an organism heterozygous for the mutation (and therefore both wild type and mutant molecular beacons indicate a 1:1 ratio); the wild type and the mutant gene are each present at one copy per cell. The skilled artisan will recognize the relationship between the organism's genotype and the expected abundance of wild type or mutant sequences, and determine whether the marker is present at one or two copies per genome.

In a further embodiment of the invention, once a genomic equivalent marker is found using methods described above or equivalent methods which identify a genomic equivalent marker, this finding may be used to identify other genomic markers without the multistep and complex task described herein of using a gene present in the population in wild type and mutant form, identifying amplicons and preparing primers and molecular beacons for each, isolating homozygous genomic DNA, determining molar extinction coefficients, and determining the ratio of wild type to mutant sequences in heterozygotes. In this further embodiment, a second genetic sequence in the genome of an organism for which a first genomic equivalent marker has been previously determined by the methods described herein is selected as a candidate genomic equivalent marker. Primers are prepared to amplify this particular candidate sequence, and a molecular beacon is prepared to identify its abundance during real-time PCR. Subsequently, a number of genomic samples are assayed for the relative abundance of the candidate genetic sequence and, concurrently, that of the previously determined genomic equivalent marker (using the above procedures). A stable ratio of abundance of the candidate sequence to the genomic equivalent sequence indicates that the candidate sequence may be used as a genomic equivalent marker, with the number of copies per genome equal to the ratio of the abundance of the candidate sequence to the predetermined genomic equivalent marker sequence. As an example, and as described in the examples below, a sequence in the CCR5 gene was first identified as a suitable genomic equivalent marker in human cells, using a mutant CCR5 allele, Δ32, to provide the determination that the gene is present at two copies per genome without pseudogenes. Subsequently, primers and a molecular beacon for the a candidate genomic equivalent marker, β-actin, were prepared, and the number of copies of the β-actin amplicon sequences was determined in a number of genomic samples. It was found that the β-actin amplicons were present at 8 times the number of CCR5 amplicons. Because CCR5 is present at two copies per genome, β-actin is therefore present at 16 copies per genome, indicating one gene and 7 pseudogenes (total of 16 alleles). Thus, β-actin may then be used as a genomic equivalent marker, using 16 copies per genome as the factor to convert β-actin amplicon abundance to cell number.

Thus, as a non-limiting example of the practice of the present invention, the abundance of the CCR5 gene or a fragment thereof in a cellular sample may be used as a marker of the number of genomes from which the sample originated. Such samples may be derived from cells from humans, other primates, or mammals that have the CCR5 gene. Samples may be derived from isolated tissues, such as blood samples, including but not limited to isolated peripheral blood mononuclear cells (PBMCs), or samples of tissue, both normal and pathologic, including tumor specimens, biopsy material, fixed and other preserved tissues, slide-mounted specimens, frozen tissue bank and blood bank material, banked or preserved germ cells, forensic samples, mummified specimens, fossilized material, and the like. The usefulness of the present invention is particularly suited to determining the abundance of a polynucleotide sequence on a per cell basis in a solid tissue samples, as it would be burdensome to accurately determine cell number in such a sample by previously available methods.

Determining the abundance of a particular sequence on a per cell basis has widely applicable utility in the diagnosing, monitoring, and application of therapeutic intervention and prevention modalities in medicine. Further, it may be used to establish epidemiological correlations in infectious and noninfectious diseases. And as mentioned above, it provides a facile method of determining cell number especially when automated instrumentation is performing the genetic analyses o a sample and can employ the same or similar programs for determining cell number and the other analytes to be measures. It is particularly suited for determining the absolute number of copies of a particular genetic sequence per cell using automated instrumentation, such as the combination of real-time PCR with molecular beacons as herein described.

One particular and non-limiting example of the utility of the present invention in providing data on nucleic acid sequence copies per cell is in the area of assessment of thymic function. The thymus gland is a major site for the production and generation of T cells which express αβ-type T cell antigen receptors (5% of the T cells are γδ). Assessment of the numbers of naive T cells in circulation in an individual, and the change in such numbers over time, provides an indication of immune recovery or reconstitution. This assessment relates to the recovery from suppression of T cells as a consequence of the effect of adverse agents, whether infectious or noninfectious, on T cells. For example, HIV-1 infection, cancer chemotherapeutic and radiotherapeutic treatments, congenital immunodeficiency syndromes, and other conditions often significantly affect the T cell population, and assessment of the recovery from or beneficial effects of treatments may be monitored by thymic function. In addition, age appears to play a role in reducing thymic function, although recent studies (for example, Douek et al., 1998, infra) have established an increase in the longevity of the active thymus than previously believed. The numbers of naive thymocytes emigrating from the thymus gland is a measure of thymic function. Methods used to assess thymic function have included imaging techniques (magnetic resonance spectroscopy, computerized axial tomography), however; these are not specific for thymic function. Whereas in certain animal species, particular thymic markers are available for recent thymic emigrants, such as the marker CHT1 in chickens, and low BRDU positive thymocytes in the mouse, no metabolic or cellular marker is known to exist. As described in the Background section above, one recently-identified measure of recent thymic emigrants found in humans is the quantity of episomal DNA circles, herein termed alpha-deletion circles (ADC) which are generated during the excisional rearrangement of T cell receptor (TCR) genes. These circles are not replicated and are passed along as cells replicate.

As described in Example 1, the CCR5 gene was found to be expressed as two copies per genome. This observation was utilized herein to enhance the utility of assays which were previously unable to or on a limited basis provide critical data on the copy number of a particular gene per cell, into a quantitative, per cell assay. Of the numerous quantitative genomic assays which may be so converted as a result of the present invention, in particular, the metholodogy utilizing molecular beacons in combination with real-time PCR provides a rapid, sensitive assay to provide both the assessment of the abundance of the target sequence(s) of interest, and , using analogous methodology, determine the copy number per cell. Such assays may be performed as separate determinations, i.,e., the nucleic acid sequence or sequences of interest and the genomic equivalent marker are determined in separate assays and the data combined and analyzed to provide the desired read-out. Alternatively, the genomic marker and one or more target nucleic acid sequences may be measured in a single assay, utilizing separately detectable molecular beacons for each target sequence and the genomic equivalent marker. As will be shown in Example VII, an assay for α1 circles and CCR5 may be performed simultaneously (multiplex), to assess total alpha circles in a nucleic acid sample. The number of different target sequences detectable is limited only by the operational characteristics of the various molecular beacons and instrumentation limitations. The skilled artisan may develop the appropriate primers and molecular beacons, or alternate methods of assessing the various targets and markers, to carry out the assay and express the results on a per cell basis.

Knowledge of the number of TCR circle sequences per cell has important diagnostic and therapeutic utility. As described above, the number of circles in a sample of nucleic acid prepared from peripheral blood mononuclear cells (PBMCs) is an indication of the number of cells of recent thymic origin. One group of patients for whom this assessment is important is in the monitoring of recovery of T cell function in HIV-infected individuals following antiviral therapy. HIV infection targets T cells, which decline during infection; effective anti-HIV therapy results in a new T cell population in the periphery. By establishing the number of thymic emigrants, the effectiveness of antiviral therapy can be assessed, and the establishment of the relationship between thymic cell numbers and duration of treatment, types and doses of single and combination therapies, and other variables related to the effectiveness of treatment and other measures of effectiveness may be used to establish correlations to aid in the management of this and other diseases.

Patients undergoing chemotherapy or radiotherapy for the treatment of dysproliferative diseases including cancer may suffer from a suppression of T cell production. Monitoring the reappearance of naive T cells in circulation using the methods described herein provides an indication of the recovery of the immune system from the various therapies. Furthermore, assessment of naive T cells using the methods of the present invention will be of benefit to individuals with thymic immunodeficiency disorders such as DiGeorge syndrome, as described above. In a further utility of the present invention, monitoring thymic function with age is useful, as recently new respect has been afforded the aging thymus.

Other examples wherein quantitation of target polynucleotide sequences on a per cell basis provides important information not previously readily obtainable is in quantitating viral, microbial or cellular (such as rearranged or recombined DNA) sequences. Some examples of viral DNA sequences are HIV-1 proviral DNA (gag and env regions) and humanherpes virus 8 or HHV-8 (ORF 25). Other examples of cellular rearranged DNA sequences are coding regions for immunoglobulin heavy chains in B-cells producing specific monoclonal antibodies.

Preparation of the sample containing nucleic acid for the method of the present invention is by conventional procedures. For example, genomic DNA may be extracted using TriReagent from Molecular Research Center, Inc., Cincinnati Ohio. Appropriate procedures applied to cell suspensions, tissues, plant material, bone, fossils, and other sources will be known by the skilled artisan.

In the practice of the present invention, the genomic equivalent marker may be utilized in a number of formats depending upon the means selected for quantitating the target sequence or sequences for which a per cell readout is desired. Such procedures range from fully automated instrumentations which simultaneously perform the quantitation of the target sequence(s) and the genomic equivalent marker, perform the calculations and express the results as copies per cell, to semiautomatic and manual procedures. A non-limiting example of a fully automated procedure is the use of molecular beacons in combination with real-time PCR, as described above. In the assay, amplification by PCR is carried out under continuous monitoring of fluorescence, in the presence of the particular primers for the target sequence(s) and genomic equivalent marker, plus molecular beacons which hybridize with the target sequences and become fluorescent. The number of thermal PCR cycles after which fluorescence of a particular molecular beacon appears (the threshold cycle) is directly related to the number of copies of the sequence in the sample, and the number of copies of the target sequence may be calculated from the threshold cycle from a standard curve in which a previously determined relationship between threshold cycle and copy number is established for each particular sequence. As mentioned above, the determinations may be made on the individual sequences separately or in a multiplex format. Determination of the number of copies per cell may be made manually or automatedly from the data acquired from the target sequence(s) and the genomic marker(s).

In a preferred embodiment, the target sequences are quantitated by real-time PCR using molecular beacons. In the particular, non-limiting example, quantitation of total alpha circles, including both α1 and α2 circles, using CCR5 as the genomic equivalent markers, may be performed. The skilled artisan will select the particular amplicon and design the appropriate primers and molecular beacons. The appropriate fluorochrome/quencher pairs for the molecular beacons may be selected based on guidance from the prior art. In one non-limiting example, the amplicons, corresponding primers and molecular beacons are as follows:

|  | α1 circle | α2 circle | CCR5 |
|---|---|---|---|
| amplicon | SEQ ID NO:5 | SEQ ID NO:9 | SEQ ID NO:1 |
| forward (5') primer | SEQ ID NO:6 (LK 157) | SEQ ID NO:6 (LK 157) | SEQ ID NO:2 (LK 46) |
| reverse (3') primer | SEQ ID NO:7 (LK 158) | SEQ ID NO:10 (J58B) | SEQ ID NO:3 (LK 47) |
| molecular beacons* | SEQ ID NO:8 (LK 159) and SEQ ID NO:11 | SEQ ID NO:8 (LK 159) | SEQ ID NO:4 (LK 155) |

*molecular beacons also include a fluorescent substituent and quencher covalently bound to the termini.

A non-limiting example of the molecular beacon to α1 and α2 circles is 5'-Fluorescein-CGAGGCGAGMCGGTGMTGMGAGCAGACAGCCTC-G-DABCYL-3' (SEQ ID NO:6). A further example of a molecular beacon for α1 circles that may be used i a multiplex format and not interfere with the CCR5 molecular beacon has a sequence as shown in SEQ ID NO:11.

A non-limiting example of the molecular beacon to CCR5 is 5'-Tetramethylrhodamine-GCGCCTATGACMGCAGCGGCAGGAGGCGC-DABCYL-3' (SEQ ID NO:11).

The above primers and molecular beacons have the following characteristics:

| Primer | length | melting temp. (C.) |
|---|---|---|
| SEQ ID NO:2 (LK 46) | 24 nt (14 G/C) | 63.0 |
| SEQ ID NO:3 (LK 47) | 24 nt (13 G/C) | 63.0 |
| SEQ ID NO:6 (LK 157) | 24 nt (14 G/C) | 63.0 |
| SEQ ID NO:7 (LK 158) | 24 nt (13 G/C) | 63.0 |
| SEQ ID NO:10 (J58B) | 26 nts | 68 C. |

| Molecular Beacon | target recognition sequence | length of arms | melting temp. of beacon (C.) | melting temp. of target (C.) |
|---|---|---|---|---|
| SEQ ID NO:4 (LK155) | 18 nt (11 G/C) + 5 nt (4 G/C) | 6 nt (5 G/C) | 71.9 | 69.9 (including 5 nt From the arms) |
| SEQ ID NO:8 (LK159) | 22 nt (11 G/C) + 6 nt (4 G/C) | 6 nt (5 G/C) | 68.3 | 69.0 (including 6 nt from the arms |

In the practice of the present invention, real-time PCR is employed with the primers and corresponding molecular beacons. The real-time PCR assay for the α1 circles, α2 circles, and CCR5 may be carried out separately, and the results of the two α circles combined and expressed per genomic equivalent, using half the number of copies of CCR5 as the number of cells. Alternatively, and in a preferred embodiment, the measurements may be performed simultaneously, wherein the fluorescence of the individual molecular beacons may be distinguished and quantitated during amplification. In this instance, the fluorescence/quenching properties of the molecular beacons must not interfere with the accurate determination of each molecular beacon in the mixture. Prior to the determination, the measurement of each of the amplicons may be standardized by running serial dilutions of each PCR generated product and determining the threshold cycle; the quantitation of the amplicons may be extrapolated from the standard curve, and the results expressed as total numbers of α circles per million PBMCs, or another appropriate denominator.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE I

ESTABLISHMENT OF THE UTILITY OF THE CCR5 GENE AS A GENOMIC EQUIVALENT MARKER

Procedures involving real-time PCR and molecular beacon were carried out as described previously (Kostrikis et al., 1998; Tyagi and Kramer; 1996). Details related to the Δ32 mutation of CCR5, and the particular primers and molecular beacons may be found in Kostrikis et al., 1998, incorporated herein by reference. A set of PCR primers were designed (SEQ ID NO:2 (LK46) and SEQ ID NO: 3 (LK47)) such that the amplicon (SEQ ID NO:1) contains the putative Δ32 deletion. The two CCR5 alleles (wild type and mutant Δ32) from human PBMCs were then amplified by PCR using the two primers and template genomic DNA from individuals who are wild type homozygotes (both CCR5 alleles are wild type) and mutant homozygotes (both CCR5 alleles have the Δ32 deletion). The amplicons from the wild type and mutant cells were subsequently purified from unincorporated mononucleotides (dNTPs) and PCR primers by either several rounds of ethanol precipitation and resuspension in water or by filtering through specialized columns purchased from QIAGEN. The molar concentration of each purified amplicon was determined by ultraviolet (UV) absorbance spectoscopy by (i) measuring the full absorbance spectra (220 to 320 nm) in a UV spectrophotometer (CARY 218), (ii) correcting for light scattering contributions at 320 nm, and (iii) assigning an extinction coefficient based on the base composition of the amplicon.

Subsequently, the correlation between the threshold cycle (derived by real time PCR [see Tyagi and Kramer, 1996, Nature Biotechnology 14:303–308] using the allele specific molecular beacons to the wild type [SEQ ID NO:12] and Δ32 mutation [SEQ ID NO: 13]) and the initial concentration of DNA templates (six log dilutions from $10^8$ to $10^2$ molecules per PCR reaction) is determined. In the particular case of the CCR5 study described herein, the two standard curves are equivalent within experimental errors, indicating that any derived threshold cycle corresponds to the same number of either wild type or mutant (Δ32) amplicons. The exactness of the two standard curves is not a critical part of the method described herein as long as the precise measurement of the abundance of the wild type and the mutant sequence is determinable in genomic samples. In this particular case, the overall thermodynamic properties and molar concentrations of the molecular beacons and PCR primers, and the length of the amplicons are the same, resulting in nearly identical standard curves, and therefore making interpretation of the ratio of the two sequences easy to visualize and interpret.

In the next and final step, the ratio of wild type CCR5 and mutant CCR5Δ32 alleles was determined in a number of samples from heterozygotes (FIG. 2). This is carried out by plotting the threshold cycles measured from the wild type and mutant alleles in each individual, using the allele-specific molecular beacons as described above. The measurement of the threshold cycle for each sequence may be measured in a single assay, using a multiplexed real time PCR molecular beacon format with the molecular beacons for the wild type and mutant alleles separately quantifiable in the sample; alternatively, they may be measured separately.

As indicated by the results in FIG. 2, the ratio of wild type CCR5 to mutant CCR5Δ32 amplicons is one to one suggesting that the CCR5 amplicon defined by the two PCR primers exist in two copies per cell. This ratio would not be achieved if any other sequences in the genome were amplified by the particular primers and identified by the molecular beacons (i.e., pseudogenes), and thus confirms the existence of only two copies per genome.

EXAMPLE II

DETERMINATION OF B-ACTIN AS A GENOMIC EQUIVALENT MARKER

By methods described above, the relative numbers of β-actin amplicons and CCR5 amplicons in duplicate genomic samples were assayed. The β-actin amplicon (SEQ ID NO: 14) was amplified using forward primer SEQ ID NO:15 and reverse primer SEQ ID NO:16, and molecular beacon with a nucleotide sequence SEQ ID NO:17. Comparison of the threshold number of β-actin to CCR5 showed the former to have a four-fold lower threshold, corresponding to a 16-fold increased abundance as compared to CCR5. This indicates that the β-actin amplicon is present at 8 times the number of CCR5 genes, or 16 per cell, of which 1 pair is the gene and 7 pairs are pseudogenes. β-actin may then be used as a genomic equivalent marker of 16 equivalents per genome.

EXAMPLE III

QUANTITATION OF HIV-1 PROVIRAL DNA ON A PER CELL BASIS

By analogous procedures to those described above, the abundance of HIV-1 provirions were assayed on a per cell basis using an amplicon to the env gene (SEQ ID NO:22), using forward (SEQ ID NO:23) and reverse (SEQ ID NO:24) primers, and molecular beacon shown in SEQ ID NO:25. The data are in Table I as follows, expressed as provirus per million PBMCs.

TABLE I

| Sample | CCR5 Eq. | HIV-1 (Env) | HIV/million PBMCs |
|---|---|---|---|
| $A_{CY}$-95CY34 | 3.29E+05 | 7 | 11 |
| B-96SH1 | 3.10E+05 | 31.00 | 50 |
| E-93TH975 | 4.60E+05 | 671.00 | 729 |
| B-92HT593 | 6.17E+05 | 4,217.00 | 3,419 |
| B-91HT651 | 3.97E+05 | 2,820.00 | 3,554 |
| B-91HT652 | 7.84E+05 | 2,132.00 | 1,360 |
| B-92US715 | 5.59E+05 | 3,846.00 | 3,441 |
| B-92US714 | 3.72E+05 | 2,617.00 | 3,520 |
| C-93MW959 | 4.21E+05 | 1,988.00 | 2,361 |
| B-91HT652 | 7.05E+05 | 2,266.00 | 1,608 |
| $A_{CY}$-95CY74 | 1.56E+05 | 107.00 | 344 |
| D-92UG021 | 2.22E+05 | 7.00 | 16 |
| E-93TH966 | 3.77E+05 | 289.00 | 383 |
| B-92HT594 | 3.22E+05 | 2,714.00 | 4,218 |
| B-92HT596 | 4.96E+05 | 2,239.00 | 2,258 |
| B-92HT599 | 3.64E+05 | 1,035.00 | |
| B-91US712 | 2.61E+05 | 525.00 | |
| B-92US711 | 1.29E+05 | 4,078.00 | |
| C-93-MW960 | 4.68E+05 | 130.00 | |

TABLE I-continued

| Sample | CCR5 Eq. | HIV-1 (Env) | HIV/million PBMCs |
|---|---|---|---|
| C-93-MW965 | 9.18E+05 | 0.00 | |
| A-92UG037 | 2.91E+05 | 130.00 | |

EXAMPLE IV

QUANTITATION OF KAPOSI'S SARCOMA VIRUS ON A PER CELL BASIS

By analogous procedures to those described above, the abundance of human herpes virus 8 (HHS-8; Kaposi's sarcoma virus) were asssayed on a per cell basis using an amplicon (SEQ ID NO:26), using forward (SEQ ID NO:27) and reverse (SEQ ID NO:28) primers, and molecular beacon shown in SEQ ID NO:29. The data are in Table 11 as follows, expressed as HHV-8 per million PBMCs.

50 μl reaction contained 5 μl [approximately 1–2 μg] of DNA and the final concentration of each component was as follows: 1.0×real-time PCR buffer containing ROX fluorophore, 3.5 mM $MgCl_2$, 0.4 pmol/μl of molecular beacon, 0.4 pmol/μl of each primer, 1.25 units of AmpliTaq Gold DNA Polymerase (Perkin-Elmer). The primers SEQ ID NO:6 (5'-GATGGAAAACACAGTGTGACATGG-3') and SEQ ID NO:7 (5'CTGTCMCAAAGGTGATGCCACAT-3') amplified a 213 bp product (SEQ ID NO:5). The molecular beacon was designed to recognize a region upstream from the signal joint. The sequence of the beacon (SEQ ID NO:8) was 5'-FAM-CGGCGTCTGCTCTTCATTCACCGTTCTCACGCCG-DABCYL-3', where FAM (6-carboxyfluorescein) serves as the reporter fluorochrome and DABCYL (4-dimethylaminophenlazobenzoic acid) the quencher. One cycle of denaturation (95° C. for 10 minutes) was performed, followed by 45 cycles of amplification (94° C. for 30 s, 60° C. for 30 s, 72° C. for 30s). PCR was carried out in a spectrofluorometric thermal cycler (ABI PRISM 7700, Applied Biosystems Inc.) that monitors changes in the

TABLE II

| No | Name | KS Status | Anti HHV8 IFA TITER | HHV-8 Eq. | CCR5 Eq. | CCR5-Δ32 Genotype | HHV-8 copies/$10^6$ cells |
|---|---|---|---|---|---|---|---|
| 1 | 4680 | CASE | HIGH | 0 | 284,083.00 | 1 | 0 |
| 2 | 7139 | CASE | LOW | 0 | 164,895.00 | 1 | 0 |
| 3 | 5019 | CASE | HIGH | 0 | 390,341.00 | 1 | 0 |
| 4 | 19977 | CASE | HIGH | 79 | 146,625.40 | 1 | 1,074 |
| 5 | 24744 | CASE | HIGH | 10.4 | 595,583.00 | 1 | 35 |
| 6 | 3097 | CASE | HIGH | 11.53 | 82,791.00 | 1 | 279 |
| 7 | 5501 | CASE | LOW | 0 | 186,259.00 | 1 | 0 |
| 8 | 4217 | CASE | HIGH | 8.26 | 555,089.00 | 1 | 30 |
| 9 | 3561 | CASE | HIGH | 0 | 137,237.00 | 1 | 0 |
| 10 | 2929 | CASE | LOW | 0 | 437,396.00 | 1 | 0 |
| 11 | 5049 | CASE | HIGH | 24.12 | 356,966.00 | 1 | 135 |
| 12 | 9205 | CASE | HIGH | 0 | 289,278.00 | 1 | 0 |
| 13 | 35822 | CASE | HIGH | 0 | 537,885.00 | 1 | 0 |
| 14 | 7212 | CASE | HIGH | 17.38 | 0.00 | 0 | |
| 15 | 8039 | CASE | LOW | 14.9 | 205,328.00 | 1 | 145 |
| 16 | 8294 | CASE | LOW | 9 | 96,744.00 | 1 | 186 |
| 17 | 31094 | CASE | HIGH | 0 | 186,367.00 | 1 | 0 |
| 18 | 31093 | CASE | LOW | 0 | 292,895.00 | 1 | 0 |
| 19 | 31112 | CASE | HIGH | 0 | 687,531.00 | 1 | 0 |
| 20 | 32964 | CASE | HIGH | 32.39 | 211,041.00 | 1 | 307 |
| 21 | 32965 | CASE | LOW | 0 | 384,445.00 | 1 | 0 |
| 22 | 33898 | CASE | HIGH | 404.77 | 148,882.00 | 2 | 2,719 |
| 23 | 8513 | CASE | LOW | 4.18 | 250,723.00 | 1 | 33 |
| 24 | 16151 | NEG | N/A | 0 | 670,958.00 | 1 | 0 |
| 25 | 36937 | NEG | N/A | 0 | 319,908.00 | 1 | 0 |
| 26 | 7820 | CASE | LOW | 15.39 | 996,557.00 | 1 | 31 |
| 27 | 14579 | NEG | N/A | 0 | 664,699.00 | 1 | 0 |
| 28 | 33304 | NEG | N/A | 0 | 559,930.00 | 1 | 0 |
| 29 | 9750 | NEG | N/A | 0 | 402,318.00 | 1 | 0 |
| 30 | 10225 | CASE | LOW | 1150.83 | 539,064.00 | 1 | 4,270 |
| 31 | 7582 | CASE | LOW | 94.29 | 202,473.00 | 1 | 931 |
| 32 | 36117 | CASE | LOW | 2608.03 | 251,977.00 | 1 | 20,701 |
| 33 | 7637 | NEG | N/A | 0 | 292,585.00 | 1 | 0 |

EXAMPLE V

QUANTITATION OF α1 CIRCLES PER CELL IN HIV-UNINFECTED AND INFECTED CHILDREN AND ADULTS

In this Example, the abundance of α1 deletion circles and CCR5 were determined by PCR amplification of the α1 deletion circle amplicon (SEQ ID NO:5) and that of CCR5 (SEQ ID NO:1). Genomic DNA from PBMCs from healthy children was extracted using TriReagent (Molecular Research Center Inc., Cincinnati, Ohio) according to the manufacturer's instructions. To detect ADC, a molecular beacon was used in combination with real-time PCR. Each fluorescence spectrum of each reaction tube during the annealing phase, while simultaneously carrying out programmed temperature cycles.

For each run, a standard curve was generated from serial dilutions of purified PCR generated product. The input copy number ranged from $10^7$ to $10^2$ copies. Copy numbers were calculated by interpolation of the experimentally determined threshold cycle as previously described (Suryanarayana et al., 1998, AIDS Res. Hum. Retroviruses 14:183–9;, Gibson et al., 1996 Genome Res. 6:995–1001; Heid et al., 1996, Genome Res. 6:986–94, quantitative PCR; Fink et al, 1998, Nature Medicine 4:1329–33).

Separately, CCR5 was quantitated in each sample following analogous procedures, using the corresponding primers (SEQ ID NO:2 AND SEQ ID NO:3) and molecular beacon (SEQ ID NO:4). The PCR conditions were identical to that used for detection of a deletion circles. For each PCR amplification (using a 96-well amplification plate), a standard curve was generated from duplicate 10×dilutions of purified CCR5 amplicons (from $10^7$ to $10^2$ copies) as previously explained. The final results were expressed as α1 deletion copies per million PBMCs.

Samples were obtained from uninfected individuals over a range of ages from under 0.3 years of age to over 95 years of age; HIV-1 infected children; acutely- and chronically-infected adults with HIV-1; and HIV-1 infected patients followed longitudinally after highly active antiretroviral therapy (HAART). In addition, α1 circles per genome were quantitated in various tissues (thymus, brain, kidney, aorta and placenta); blood (CD-4N, CD-4M, CD-8N, CD-8M, B-cells and cells from DiGeorge/scid patient), and in several cell lines.

Figure 8:
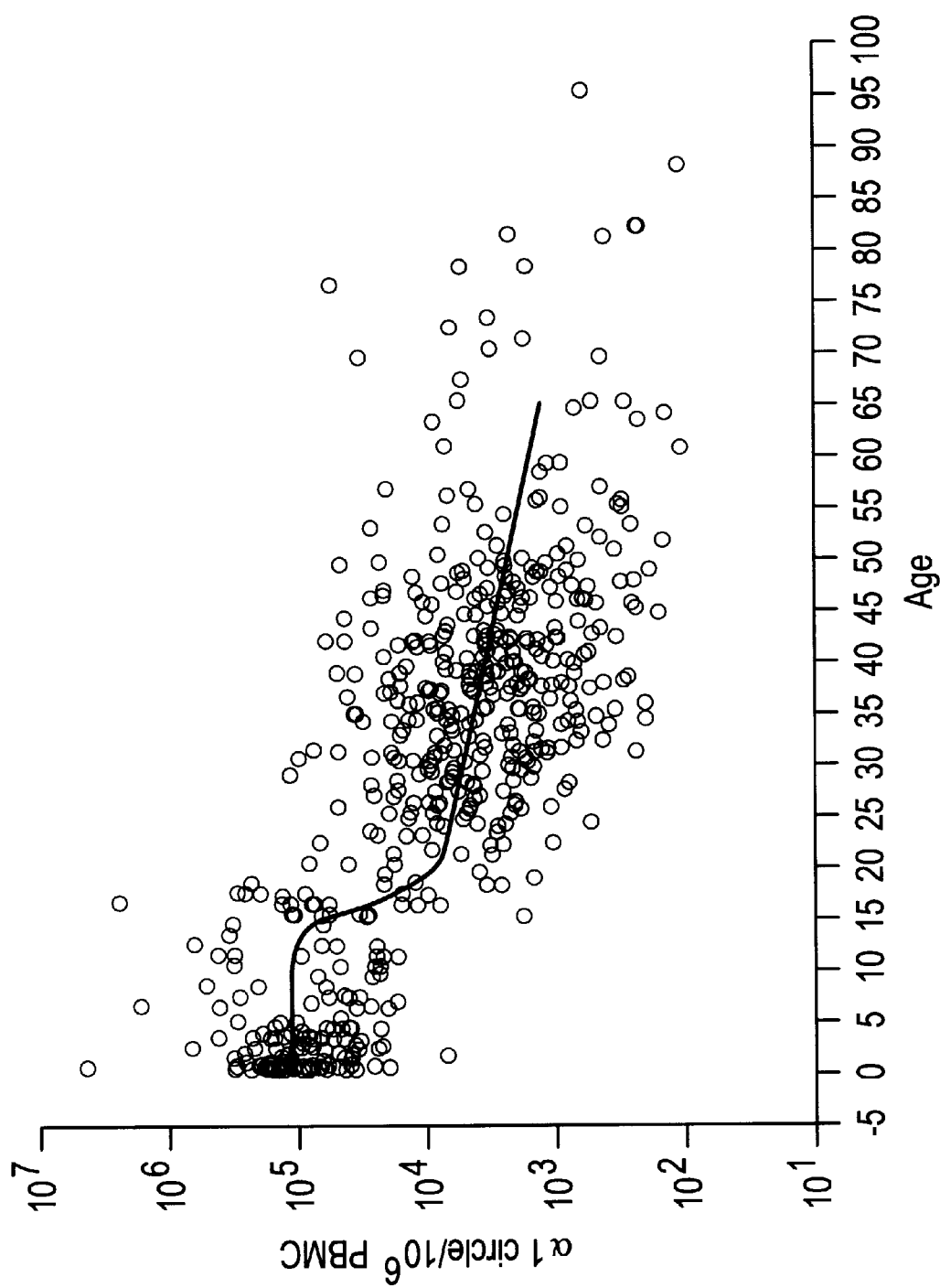
FIG. 8 depicts the al circle number per million PBMCs with age.

Examples of data from uninfected individuals is shown in Table III, and the data plotted in FIG. 8.

TABLE III

| age | α1 copies/$10^6$ PBMC |
|---|---|
| 0–0.3 | 227754 |
| 0–0.3 | 140704 |
| 0–0.3 | 91242 |
| 0–0.3 | 85394 |
| 0–0.3 | 20314 |
| 0.3–5 | 188005 |
| 0.3–5 | 158502 |
| 0.3–5 | 128289 |
| 0.3–5 | 249790 |
| 0.3–5 | 78026 |
| 6–10 | 102082 |
| 6–10 | 146914 |
| 6–10 | 60634 |
| 6–10 | 33452 |
| 6–10 | 214493 |
| 11–15 | 93815 |
| 11–15 | 306009 |
| 11–15 | 418654 |
| 11–15 | 24225 |
| 11–15 | 637718 |
| 16–20 | 76917 |
| 16–20 | 73883 |
| 16–20 | 131084 |
| 16–20 | 132466 |
| 16–20 | 15524 |
| 21–25 | 9225 |
| 21–25 | 3212 |
| 21–25 | 2587 |
| 21–25 | 67648 |
| 21–25 | 1063 |
| 26–30 | 3950 |
| 26–30 | 8773 |
| 26–30 | 5740 |
| 26–30 | 16908 |
| 26–30 | 2548 |
| 31–35 | 8858 |
| 31–35 | 19132 |
| 31–35 | 49347 |
| 31–35 | 1192 |
| 31–35 | 76617 |
| 36–40 | 3168 |
| 36–40 | 21818 |
| 36–40 | 2462 |
| 36–40 | 19357 |
| 36–40 | 8282 |
| 41–45 | 12261 |
| 41–45 | 9536 |
| 41–45 | 17051 |
| 41–45 | 1226 |
| 41–45 | 3620 |
| 46–50 | 2637 |
| 46–50 | 22602 |
| 46–50 | 4006 |
| 46–50 | 12631 |
| 46–50 | 6167 |
| 51–55 | 1891 |
| 51–55 | 8536 |
| 51–55 | 1019 |
| 51–55 | 369 |
| 51–55 | 872 |
| 55+ | 2498 |
| 55+ | 463 |
| 55+ | 252 |
| 55+ | 259 |
| 55+ | 699 |

α1 Circles per million PBMCs were determined in chronically infected HIV-1 patents, with the results on a subset of patients shown below in Table IV as an example of the determination of threshold cycles for α1 circles and CCR5, and the expression of the results in α1 circles per million PBMCs.

TABLE IV

| Chronically infected patients | α 1 circle threshold cycle | α 1 copies | CCR5 threshold cycle | CCR5 copies | copies/ $10^5$ PBM |
|---|---|---|---|---|---|
| patient1 | 29.62 | 2630 | 22.79 | 3.90E + 06 | 1.35E + 0 |
| patient2 | 35.77 | 42 | 26.14 | 3.66E + 05 | 2.28E + 0 |
| patient3 | 37.65 | 12 | 28.67 | 6.13E + 04 | 3.85E + 0 |
| patient4 | 35.25 | 59 | 25.91 | 4.31E + 05 | 2.76E + 0 |
| patient5 | 32.12 | 489 | 23.32 | 2.69E + 06 | 3.64E + 0 |

In a further demonstration of the utility of the present invention, α1 circles per million PBMCs were determined in chronically and acutely infected HIV-1 patients, as shown in Table V.

TABLE V

| Chronically infected patients (no treatment) | | |
|---|---|---|
| | age | Alpha1 circle/$10^5$ PBMC |
| Patient1 | 32 | 9192 |
| patient2 | 53 | 2470 |
| patient3 | 58 | 338 |
| patient4 | 50 | 50 |
| patient5 | 26 | 1742 |
| Acutely infected patients (no treatment) | | |
| | age | Alpha1 circle/$10^6$ PBMC |
| patient6 | 32 | 15092 |
| patient7 | 48 | 7087 |
| patient8 | 36 | 1657 |
| patient9 | 25 | 20960 |
| patient10 | 39 | 56396 |

Figure 6:
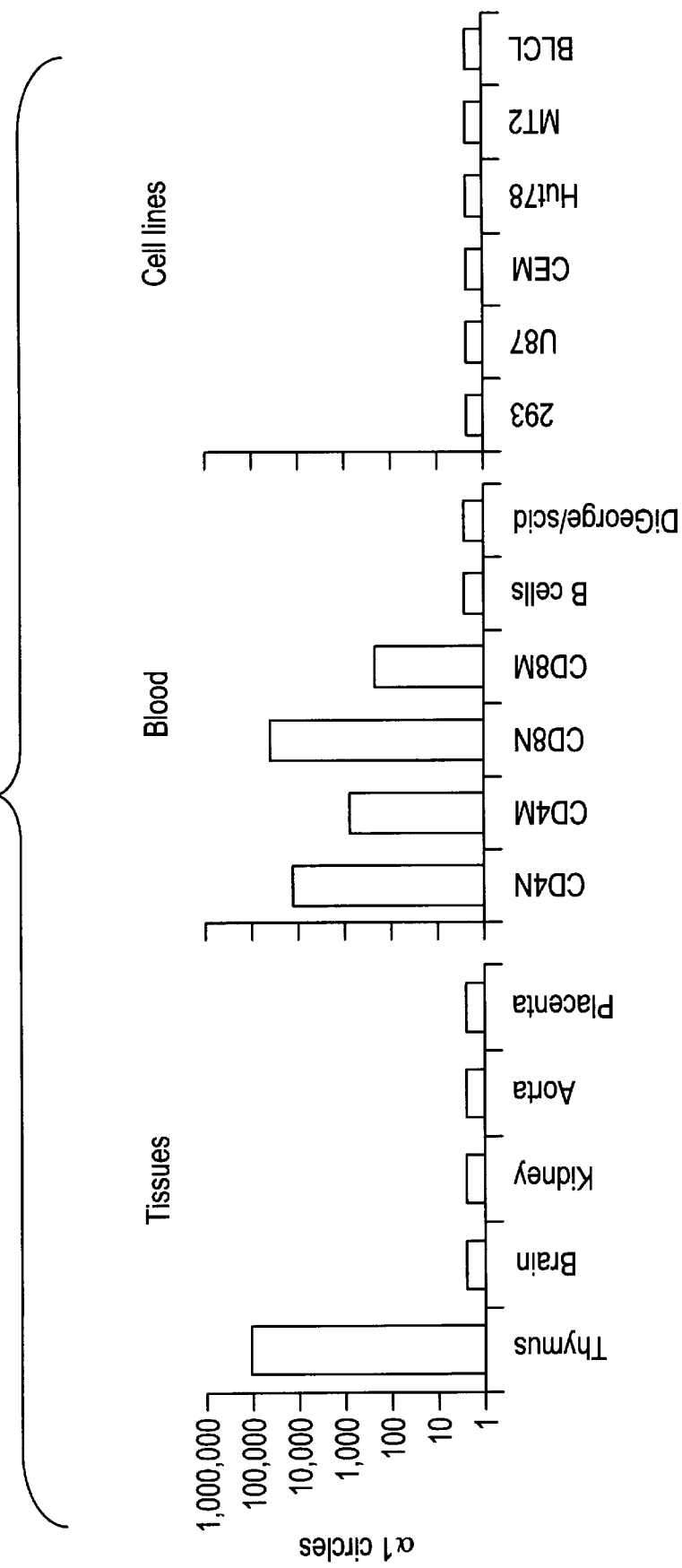
FIG. 6 depicts the specificity of al circles in various tissues, blood, and cell lines.

As shown in FIG. 6, of the various solid tissues tested, α1 circles are found only in thymus. In blood cells, they are present in the various T cell populations assayed, but not in B-cells nor in cells from 4 DiGeorge syndrome patient. Cell lines showed no α1 circles, as the circles would be diluted out over many generations since the generation of TCR.

Figure 7:
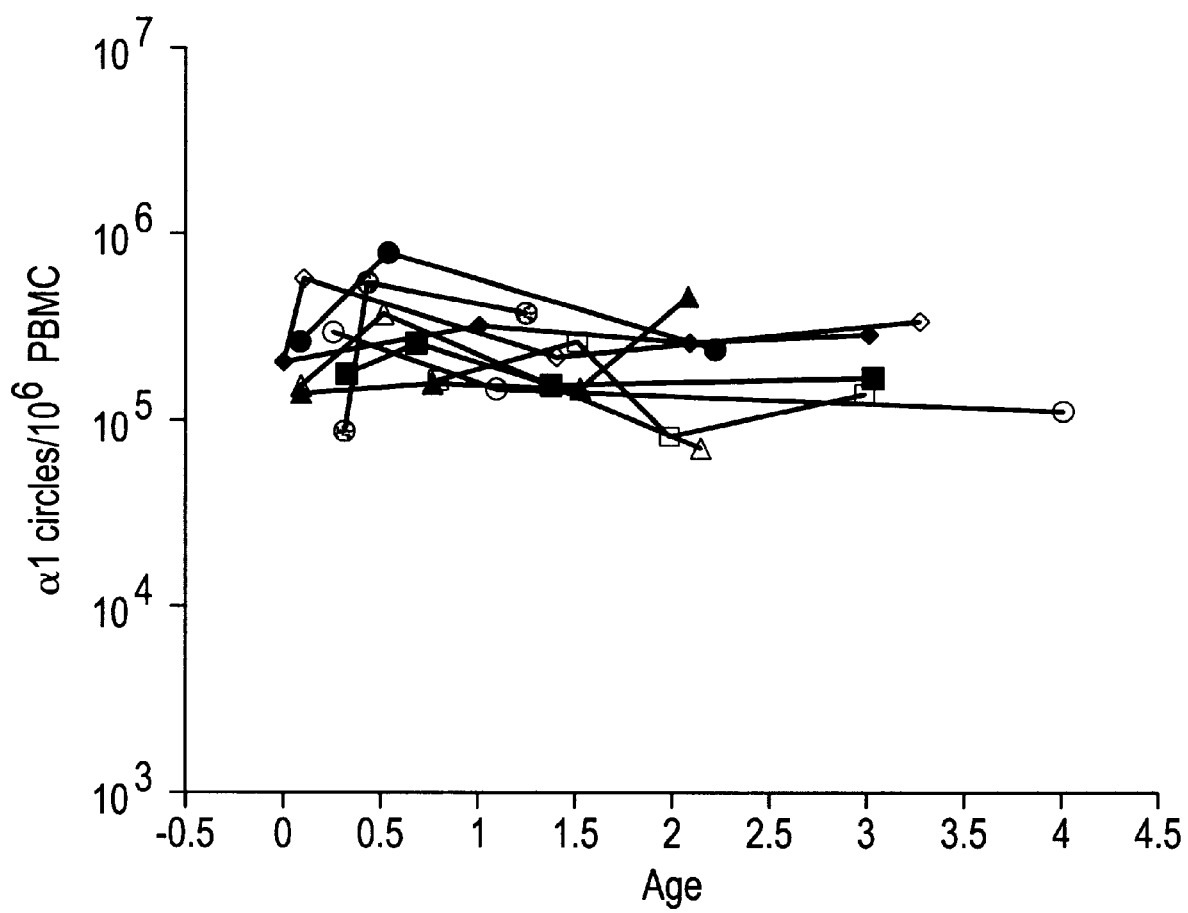
FIG. 7 depicts the al circle number per million PBMCs in HIV-uninfected children followed longitudinally.
Figure 10:
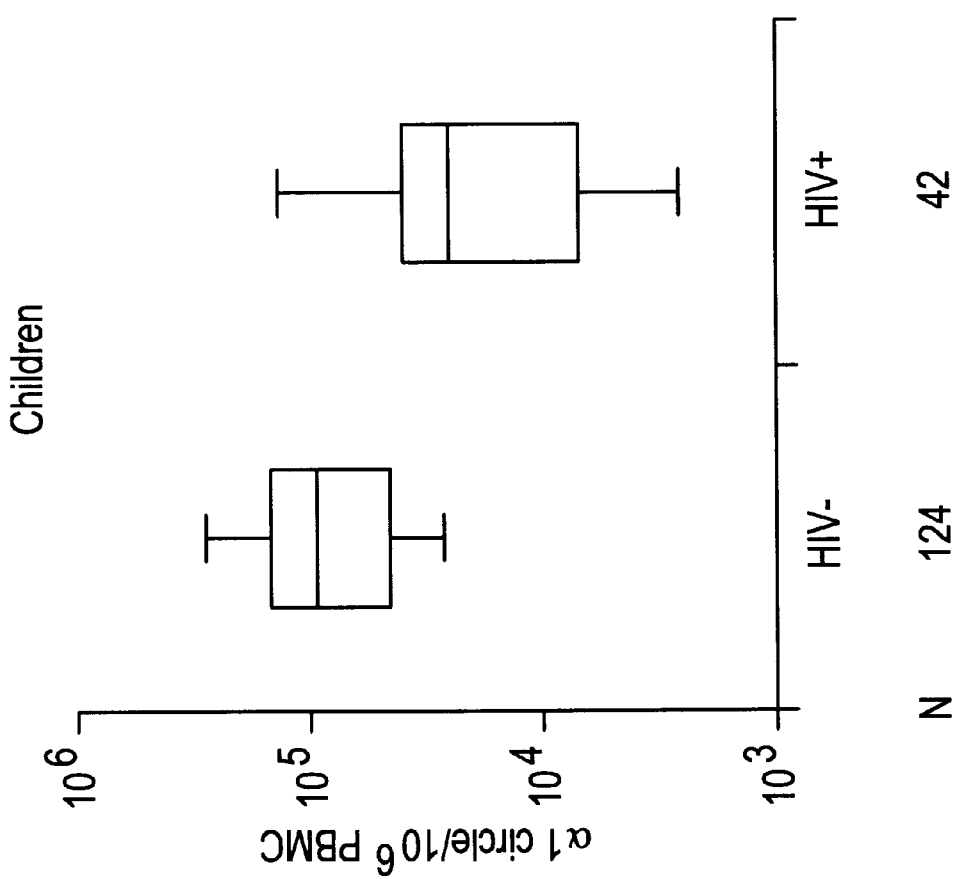
FIG. 10 shows the impact of HIV on α1 circles per million PBMCs in children.
Figure 9:
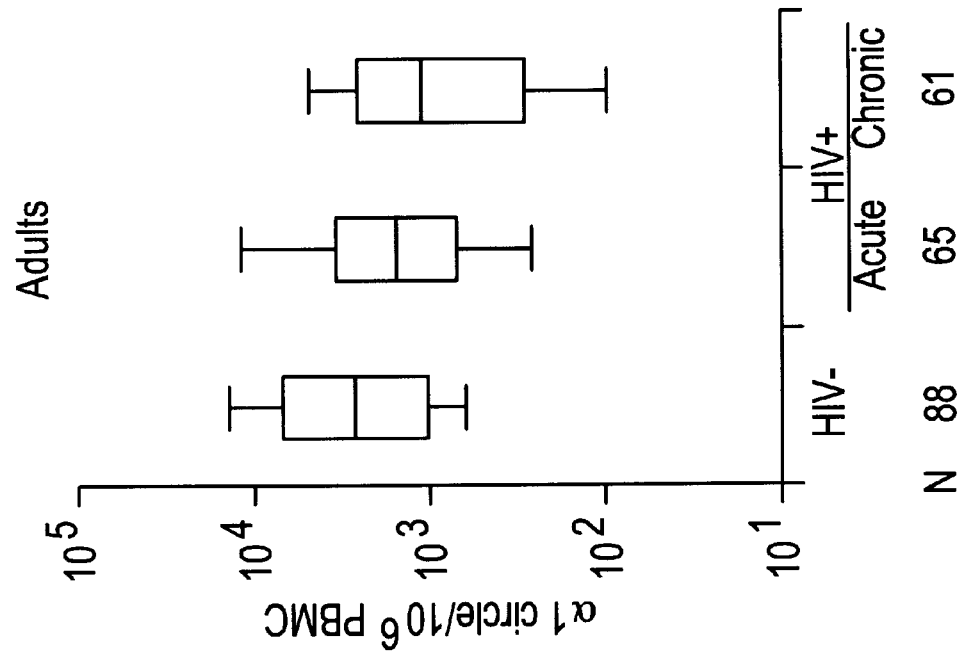
FIG. 9 shows the impact of HIV-1 infection on recent thymic emigrants expressed as α1 circles per million PBMC in uninfected, acutely and chronically infected individuals.

In HIV-1-uninfected individuals, recent thymic emigrants as assessed by α1 circles per million PBMCs showed a stable level during the first decade of life. It then declines sharply in the late teen years, followed by a slow decrease after the 20s (FIG. 8). HIV-1-uninfected children (ages 0 to 4) followed longitudinally showed no decline in thymic function (FIG. 7). HIV infection results in a lower concentration of recent thymic emigrants in a subset of patients, but not in all (FIG. 9); infected children show the greatest difference (FIG. 10). HAART results in significant increases in recent thymic emigrants primarily in those with an existing impairment (FIG. 11) Patients with low baseline levels of α1 circles (<2200 per million PBMCs) showed the largest increase in α1 circles after treatment.

EXAMPLE VI

Multiplex assay for α1 circles and CCR5

In a further embodiment of the present invention, the assays for the target polynucleotide sequence(s) and the genomic equivalent marker(s) may be performed in a single assay, referred to herein as multiplex format, comprising the sample and all of the necessary PCR reagents, primers, and molecular beacons; the assay performed in an instrument which carries out the thermal cycling and monitoring of fluorescence at all of the necessary wavelengths to assess the appearance of the various molecular beacons' signals during the amplification process. To assay α1 using CCR5 as the genomic equivalent marker, the assay conditions are as follows (component, amount per reaction):genomic DNA, 5.0 μl; 10×TaqMan Buffer A, 5.0 μl; dNTPs (10 mM), 4.0 μl; MgCl$_2$(25 mM), 7.0 μl, LK157 (20 pmole/μl), 1.0 μl; LK158 (20 pmole/μl), 1.0 μl; LK46 (20 pmole/μl), 1.0 μl; LK47 (20 pmole/μl), 1.0 μl; LK159-FAM Beacon, 0.5 μl; LK155-TET Beacon; 1.0 μl; AmpliTaq Gold Polymerase; 0.5 μl; and dH$_2$O; 23.0 μl. A series of standards of both CCR5 and α1 circles were prepared at $10^1$ to $10^6$ copies per 5 μl; 5 μl per assay provides $10^1$ to $10^6$ copies, respectively, of CCR5 and α1 circles per PCR reaction.

Real-time PCR was run with under the following parameters: 1 cycle at 94 C for 10 minutes: 45 cycles of: 94 C for 15 sec followed by 60 C for 30 seconds, during which fluorescence data is collected, followed by 72 C for 30 seconds. CT refers to threshold cycle.

Results are shown in Table VI:

TABLE VI

| Sample ID | CCR5 CT | CCR5 Eq. | Alpha1 CT | Alpha1 Eq. | Cell Eq. | Alpha1 Eq./million cell Eq. |
|---|---|---|---|---|---|---|
| A1 | 26.1 | 1,200,000 | 34.69 | 1,700.0 | 600,000 | 2,833 |
| A2 | 26.93 | 630,000 | 35.82 | 800.0 | 315,000 | 2,540 |
| A3 | 27.83 | 310,000 | 36.42 | 540.0 | 155,000 | 3,484 |
| A4 | 29.1 | 110,000 | 36.76 | 430.0 | 55,000 | 7,818 |
| A5 | 30.36 | 41,000 | 38.79 | 110.0 | 20,500 | 5,366 |
| A6 | 31.3 | 19,000 | 41.3 | 21.0 | 9,500 | 2,211 |
| A7 | 31.87 | 12,000 | 45 | | 6,000 | 0 |
| A8 | 33.15 | 4,400 | 45 | 0.0 | 2,200 | 0 |
| B1 | 26.04 | 1,300,000 | 34.65 | 1,800.0 | 650,000 | 2,769 |
| B2 | 26.66 | 790,000 | 35.77 | 830.0 | 395,000 | 2,101 |
| B3 | 27.94 | 280,000 | 36.37 | 560.0 | 140,000 | 4,000 |
| B4 | 28.79 | 140,000 | 37.59 | 250.0 | 70,000 | 3,571 |
| B5 | 30.19 | 47,000 | 37.84 | 210.0 | 23,500 | 8,936 |
| B6 | 31.08 | 23,000 | 40.13 | 46.0 | 11,500 | 4,000 |
| B7 | 32.11 | 10,000 | 40.75 | 30.0 | 5,000 | 6,000 |
| B8 | 33.08 | 4,600 | 42.43 | 9.8 | 2,300 | 4,261 |
| C1 | 26.07 | 1,300,000 | 34.89 | 1,500.0 | 650,000 | 2,308 |
| C2 | 26.76 | 730,000 | 35.22 | 1,200.0 | 365,000 | 3,288 |
| C3 | 27.77 | 330,000 | 36.64 | 460.0 | 165,000 | 2,788 |
| C4 | 28.87 | 130,000 | 37.47 | 270.0 | 65,000 | 4,154 |
| C5 | 29.79 | 64,000 | 38.92 | 100.0 | 32,000 | 3,125 |
| C6 | 31.33 | 19,000 | 40.85 | 28.0 | 9,500 | 2,947 |
| C7 | 31.85 | 12,000 | 40.61 | 33.0 | 6,000 | 5,500 |
| C8 | 32.85 | 5,500 | 41.56 | 18.0 | 2,750 | 6,545 |
| D1 | 26.01 | 1,300,000 | 35.01 | 1,400.0 | 650,000 | 2,154 |
| D2 | 26.91 | 650,000 | 35.46 | 1,000.0 | 325,000 | 3,077 |
| D3 | 27.95 | 280,000 | 36.54 | 500.0 | 140,000 | 3,571 |
| D4 | 28.87 | 130,000 | 37.32 | 300.0 | 65,000 | 4,615 |
| D5 | 29.96 | 56,000 | 37.94 | 200.0 | 28,000 | 7,143 |
| D6 | 31.16 | 21,000 | 38.96 | 99.0 | 10,500 | 9,429 |
| D7 | 31.95 | 11,000 | 43.66 | 4.3 | 5,500 | 782 |
| D8 | 32.95 | 5,100 | 42.59 | 8.8 | 2,550 | 3,451 |

EXAMPLE VII

QUANTIFICATION OF α2 CIRCLES IN HUMAN PBMCS

Procedures were analogous to the detection of α1 circles as described in Example II above with the exception that the reverse primer used is SEQ ID NO:10 (J58B). The rest of the reagents and conditions are the same.

The results are shown in Table VII:

TABLE VII

| Sample ID | CCR5 CT | CCR5 Eq. | Alpha2 CT | Alpha2 Eq. | Cell Eq. | Alpha Eq./million cell Eq. |
|---|---|---|---|---|---|---|
| A1 | 26.1 | 1,200,000 | 37.47 | 160 | 600,000 | 267 |
| A2 | 26.93 | 630,000 | 38.74 | 62 | 315,000 | 197 |
| A3 | 27.83 | 310,000 | 38.78 | 60 | 155,000 | 387 |
| A4 | 29.1 | 110,000 | 40.09 | 23 | 55,000 | 418 |
| A5 | 30.36 | 41,000 | 40.52 | 17 | 20,500 | 829 |
| A6 | 31.3 | 19,000 | 41.73 | 7 | 9,500 | 726 |
| A7 | 31.87 | 12,000 | 45 | | 6,000 | 0 |
| A8 | 33.15 | 4,400 | 45 | | 2,200 | 0 |
| B1 | 26.04 | 1,300,000 | 36.86 | 250 | 650,000 | 385 |
| B2 | 26.66 | 790,000 | 38.71 | 64 | 395,000 | 162 |
| B3 | 27.94 | 280,000 | 37.99 | 110 | 140,000 | 786 |
| 84 | 28.79 | 140,000 | 40.52 | 17 | 70,000 | 243 |
| B5 | 30.19 | 47,000 | 40.25 | 20 | 23,500 | 851 |
| B6 | 31.08 | 23,000 | 40.19 | 21 | 11,500 | 1,826 |
| B7 | 32.11 | 10,000 | 42.8 | 3 | 5,000 | 620 |
| B8 | 33.08 | 4,600 | 45 | | 2,300 | 0 |
| C1 | 26.07 | 1,300,000 | 36.79 | 260 | 650,000 | 400 |
| C2 | 26.76 | 730,000 | 37.82 | 120 | 365,000 | 329 |
| C3 | 27.77 | 330,000 | 38.74 | 62 | 165,000 | 376 |
| C4 | 28.87 | 130,000 | 40.3 | 20 | 65,000 | 308 |
| C5 | 29.79 | 64,000 | 45 | | 32,000 | 0 |
| C6 | 31.33 | 19,000 | 43.4 | 2 | 9,500 | 211 |
| C7 | 31.85 | 12,000 | 45 | | 6,000 | 0 |
| C8 | 32.85 | 5,500 | 45 | | 2,750 | 0 |
| D1 | 26.01 | 1,300,000 | 37.01 | 220 | 650,000 | 338 |
| D2 | 26.91 | 650,000 | 38.58 | 70 | 325,000 | 215 |
| D3 | 27.95 | 280,000 | 39.31 | 41 | 140,000 | 293 |
| D4 | 28.87 | 130,000 | 45 | | 65,000 | 0 |
| D5 | 29.96 | 56,000 | 45 | | 28,000 | 0 |
| D6 | 31.16 | 21,000 | 42.97 | 3 | 10,500 | 267 |
| D7 | 31.95 | 11,000 | 41.09 | 11 | 5,500 | 2,000 |

EXAMPLE VIII

MULTIPLEX QUANTITATION OF α1 and α2 CIRCLES PER CELL

By analogy to the foregoing examples, a multiplex assay may be prepared which combines measurements of α1 circles, α2 circles, and CCR5 into a single real-time PCR run. As described in the Example above, the α2 circle is detected with the same molecular beacon and forward primer as α1, and a different reverse primer. As a single beacon is used for the detection of both circles, the results indicate the total abundance of a circles in the sample. The components in the PCR reaction for the unique and common primers and beacon for α2 are increased to account for the ca. 15% abundance of α2 circles as compared to α1. The fluorescences of the two molecular beacons are measured simultaneously, and based on a previously run standard curves for the amplicons (as described in the Examples above), the combined abundance α1 and α2 circles per cell is calculated and expressed per cell using CCR5 as the genomic equivalent marker.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for determining in a nucleic acid sample of cellular origin the number of copies per cell of at least one preselected polynucleotide target sequence, comprising quantifying in said sample the abundance of said at least one target sequence, quantifying in said sample the abundance of at least one genomic equivalent marker sequence, and expressing said number of copies of said at least one target sequence per cell as a ratio between said abundance of said target sequence and said abundance of said at least one genomic equivalent marker.

2. The method of claim 1 wherein said genomic equivalent marker is selected from the group consisting of CCR5 and β-actin.

3. The method of claim 1 wherein said genomic equivalent marker is CCR5.

4. The method of claim 1 wherein said quantifying of said at least one target sequence and of said at least one genomic equivalent marker sequence is performed using real-time PCR amplification in combination with molecular beacons.

5. The method of claim 4 wherein said at least one genomic equivalent marker is CCR5.

6. The method of claim 5 wherein said quantifying of CCR5 is performed using amplification primers SEQ ID NO:2 and SEQ ID NO:3.

7. The method of claim 5 wherein said quantifying of CCR5 is performed using a molecular beacon with a sequence of SEQ ID NO:4.

8. The method of claim 7 wherein said molecular beacon is Tetramethylrhodamine-GCGCCTATGACAAGCAGCGGCAGGAGGCGC-DABCYL SEQ ID NO:4.

9. The method of claim 1 wherein said target sequence is a marker of thymocyte proliferation.

10. The method of claim 9 wherein said marker of thymocyte proliferation is a T cell receptor gene DNA deletion circle.

11. The method of claim 10 wherein said T cell receptor circle is selected from the group consisting of α1 circles, α2 circles, δ1 circles, δ2 circles, δ3 circles, δ4 circles, δ5 circles, and combinations thereof.

12. The method of claim 10 wherein said T cell receptor circle is selected from the group consisting of α1 circles, α2 circles, and combinations thereof.

13. The method of claim 12 wherein said quantifying of α1 circles is performed using primers SEQ ID NO:6 and SEQ ID NO:7 and a molecular beacon with a sequence of SEQ ID NO:8.

14. The method of claim 13 wherein said molecular beacon is Fluorescein-CGAGGCGAGMCGGTGAATGMGAGCAGACAGCCT-CGDABCYL SEQ ID NO:4.

15. The method of claim 12 wherein said quantifying of α2 circles is performed using primers SEQ ID NO:6 and SEQ ID NO:10 and a molecular beacon with a sequence of SEQ ID NO:8.

16. The method of claim 1 wherein said target sequence is a pathogen.

17. The method of claim 1 wherein said quantification of said at least one target sequence is determined by a method selected from the group consisting of real-time PCR and competitive PCR.

18. The method of claim 1 wherein said quantifying of said at least one target sequence and said quantifying of said at least one genomic equivalent marker are performed simultaneously.

19. The method of claim 1 wherein said at least one target sequence is DNA.

20. A method for determining in a nucleic acid sample of cellular origin the number of copies per cell of at least one preselected polynucleotide target sequence, comprising the steps of:

a. providing a nucleic acid sample derived from a sample of cellular origin in which said determining the number of copies per cell is desired;

b. providing forward and reverse primers for each of said at least one target sequences and said at least one genomic marker sequence;

c. providing a molecular beacon capable of binding to a subsequence within the target sequence for each of said at least one target sequence and said at least one genomic equivalent marker sequence;

d. incubating said nucleic acid sample, said primers and said molecular beacons together with the necessary components and under real-time PCR conditions to amplify said at least one target sequence and said at least one genomic equivalent marker sequence and to cause the interaction between said molecular beacons and said sequences present in said sample;

e. monitoring the change in fluorescence with time of each of said molecular beacons during said real-time PCR;

f. quantitating the abundance of any of said at least one target sequence in said sample and the abundance of said at least one genomic equivalent marker sequence by correlating the threshold cycle of each molecular beacon with a predetermined relationship between the threshold cycle and the quantity of the sequence; and g. expressing the number of copies of said at least one target sequence per cell as the ratio of the abundance of said at least one target sequence with the abundance of said at least one genomic equivalent marker.

21. The method of claim 20 wherein said at least one target sequence is α1 deletion circles and said at least one genomic equivalent marker is CCR5.

22. The method of claim 21 wherein said primers for α1 circles are SEQ ID NO:6 and SEQ ID NO:7, said α1 molecular beacon is Fluorescein-CGAGGCGAGMCGGTGMTGAAGAGCAGACAGCCT-CG-DABCYL SEQ ID NO:8, said CCR5 primers are SEQ ID NO: 2 and SEQ ID NO:3, and said CCR5 molecular beacon is Tetramethylrhodamine-GCGCCTATGACAAGCAGCGGCAGGAGGCGC-DABCYL SEQ ID NO:4.

* * * * *

SEQUENCE LISTING

```
<160> NUMBER OF SEQ ID NOS:  29

<210> SEQ ID NO: 1
<211> LENGTH: 239
<212> TYPE: DNA
<213> ORGANISM: Homo sapien

<400> SEQUENCE: 1
gctgtgtttg cgtctctccc aggaatcatc tttaccagat ctcaaaaaga aggtcttcat      60
tacacctgca gctctcattt tccatacagt cagtatcaat tctggaagaa tttccagaca    120
ttaaagatag tcatcttggg gctggtcctg ccgctgcttg tcatggtcat ctgctactcg    180
ggaatcctaa aaactctgct tcggtgtcga aatgagaaga agaggcacag ggctgtgag     239

<210> SEQ ID NO: 2
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 2
gctgtgtttg cgtctctccc agga                                            24

<210> SEQ ID NO: 3
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 3
ctcacagccc tgtgcctctt cttc                                            24

<210> SEQ ID NO: 4
<211> LENGTH: 30
<212> TYPE: DNA
<213> ORGANISM: Homo sapien

<400> SEQUENCE: 4
gcgcctatga caagcagcgg caggaggcgc                                      30

<210> SEQ ID NO: 5
<211> LENGTH: 208
<212> TYPE: DNA
<213> ORGANISM: Homo sapien

<400> SEQUENCE: 5
gatggaaaac acagtgtgac atggagggct gaacttattg caactcgtga gaacggtgaa     60
tgaagagcag acagggcccg tgccagctgc agggtttagg cacggggtgc aggtgcctat    120
```

-continued

```
gcatcaccgt gcacaggagt gggcaccttt acaaaaacca gaggtgtcag catggttgaa      180
agggatgtgg catcaccttt gttgacag                                         208
```

<210> SEQ ID NO: 6
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 6

```
gatggaaaac acagtgtgac atgg                                             24
```

<210> SEQ ID NO: 7
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 7

```
ctgtcaacaa aggtgatgcc acat                                             24
```

<210> SEQ ID NO: 8
<211> LENGTH: 37
<212> TYPE: DNA
<213> ORGANISM: Homo sapien

<400> SEQUENCE: 8

```
cgaggcgaga acggtgaatg aagagcagac agcctcg                               37
```

<210> SEQ ID NO: 9
<211> LENGTH: 293
<212> TYPE: DNA
<213> ORGANISM: Homo sapien

<400> SEQUENCE: 9

```
ggatggaaaa cacagtgtga catggagggc tgaacttatt gcaactcgtg agaacggtga      60
atgaagagca gacagggccc gtgccagctg cagggtttag gcacggggtg caggtgccta     120
tgcatcaccg tgcactgtgc tgagggggctt tgcaaaaacc tgtggcatca gcttaacgaa    180
ccctgctttg cagagcttcc caagaactag aattttttctc caacttctaa gctttagagg    240
aaggataagt catggtatct ttctttccag tagcctaggg cttcaggcct gac            293
```

<210> SEQ ID NO: 10
<211> LENGTH: 26
<212> TYPE: DNA
<213> ORGANISM: Artificial Sequence
<220> FEATURE:
<223> OTHER INFORMATION: Description of Artificial Sequence: PRIMER

<400> SEQUENCE: 10

```
gtcaggcctg aagccctagg ctactg                                           26
```

<210> SEQ ID NO: 11
<211> LENGTH: 34
<212> TYPE: DNA
<213> ORGANISM: Homo sapien

<400> SEQUENCE: 11

```
cggcgtctgc tcttcattca ccgttctcac gccg                                  34
```

```
<210> SEQ ID NO: 12
<211> LENGTH: 37
<212> TYPE: DNA
<213> ORGANISM: Homo sapien

<400> SEQUENCE: 12
ccggtctgga aattcttcca gaattgatac tgaccgg                              37

<210> SEQ ID NO: 13
<211> LENGTH: 33
<212> TYPE: DNA
<213> ORGANISM: Homo sapien

<400> SEQUENCE: 13
cggctatctt taatgtatgg aaaatgagag ccg                                  33

<210> SEQ ID NO: 14
<211> LENGTH: 279
<212> TYPE: DNA
<213> ORGANISM: Homo sapien

<400> SEQUENCE: 14
tcacccacac tgtgcccatc tacgagggt atgccctccc ccatgccatc ctgcgtctgg      60
acctggctgg cccggacctg actgactacc tcatgaagat cctcaccgag cgcggctaca   120
gcttccacca cacggccgag cgggaaatcg tgcgtgacat taacgagaag ctgtgctacg   180 tcgcctgga cttcgagcaa gagatggcca cggctgcttc cagctcctcc ctggagaaga   240
gctacgagct gcctgacggc caggtcatca ccattggca                          279

<210> SEQ ID NO: 15
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 15
tcacccacac tgtgcccatc tacg                                           24

<210> SEQ ID NO: 16
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 16
tgccaatggt gatgacctgg ccgt                                           24

<210> SEQ ID NO: 17
<211> LENGTH: 37
<212> TYPE: DNA
<213> ORGANISM: Homo sapien

<400> SEQUENCE: 17
ccggtcagcc gtggccatct cttgctcgaa ggaccgg                             37

<210> SEQ ID NO: 18
<211> LENGTH: 250
<212> TYPE: DNA
<213> ORGANISM: Homo sapien

<400> SEQUENCE: 18
```

```
actagcggag gctagaagga gagagacatg ggtgcgagag cgtcagtatt aagcggggga      60
gaattagata gatgggaaaa aattcggtta aggccagggg gaaagaaaaa atataaatta     120
aaacatatag tatgggcaag cagggagcta gaacgattcg cagttaatcc tggcctgtta    180
gaaacatcag aaggctgtag acaaatactg ggacagctac aaccatccct tcagacagga   240
tcagaagaac                                                            250

<210> SEQ ID NO: 19
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 19
actagcggag gctagaagga gaga                                             24

<210> SEQ ID NO: 20
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 20
gttcttctga tcctgtctga aggg                                             24

<210> SEQ ID NO: 21
<211> LENGTH: 37
<212> TYPE: DNA
<213> ORGANISM: Homo sapien

<400> SEQUENCE: 21
ccggtctccc ccgcttaata ctgacgctct cgaccgg                               37

<210> SEQ ID NO: 22
<211> LENGTH: 274
<212> TYPE: DNA
<213> ORGANISM: Homo sapien

<400> SEQUENCE: 22
ttcttgggag cagcaggaag cactatgggc gcagcgtcaa tgacgctgac ggtacaggcc      60
agacaattat tgtctggtat agtgcaacag cagaacaatt tgctgagggc tattgaggcg    120
caacagcatc tgttgcaact cacagtctgg ggcatcaagc agctccaggc aagagtcctg    180
gctgtggaaa gatacctaaa ggatcaacag ctcctgggga tttggggttg ctctggaaaa   240
ctcatttgca ccactgctgt gccttggaat gcta                                 274

<210> SEQ ID NO: 23
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 23
ttcttgggag cagcaggaag cact                                             24

<210> SEQ ID NO: 24
<211> LENGTH: 24
<212> TYPE: DNA
<213> ORGANISM: Artificial Sequence
```

```
<220> FEATURE:
<223> OTHER INFORMATION: Description of Artificial Sequence: PRIMER

<400> SEQUENCE: 24
tagcattcca aggcacagca gtgg                                              24

<210> SEQ ID NO: 25
<211> LENGTH: 37
<212> TYPE: DNA
<213> ORGANISM: Homo sapien

<400> SEQUENCE: 25
ccggtctctt gcctggagct gcttgatgcc cgaccgg                                37

<210> SEQ ID NO: 26
<211> LENGTH: 261
<212> TYPE: DNA
<213> ORGANISM: Homo sapien

<400> SEQUENCE: 26
gcaacgtcag atgtgaccgg cgtgggaatt atctcgcagg ttgccagctg accatgactc       60
aaaccgggca ggttctcgca gcgaggaacc ccagcagtgt atcccacgtg atccattctg      120
tttcccggtg agccggtttg cacgcccgct ttcattttga tatagtcatg cagctggcgg      180
tcctgatacg cgtcccctgg gaaaatcata aagaggtcct gacaatgtac tcccatgtct      240
gtagttatgg cggccacgtg g                                                261

<210> SEQ ID NO: 27
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 27
gcaacgtcag atgtgaccgg cgtg                                              24

<210> SEQ ID NO: 28
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 28
ccacgtggcc gccataacta caga                                              24

<210> SEQ ID NO: 29
<211> LENGTH: 34
<212> TYPE: DNA
<213> ORGANISM: Homo sapien

<400> SEQUENCE: 29
cccgcatgga tcacgtggga tacactgctg cggg                                   34
```